United States Patent
Gozzini et al.

(10) Patent No.: US 10,360,431 B2
(45) Date of Patent: Jul. 23, 2019

(54) ELECTRONIC DEVICE INCLUDING PIN HOLE ARRAY MASK ABOVE OPTICAL IMAGE SENSOR AND RELATED METHODS

(71) Applicant: Apple Inc., Cupertino, CA (US)

(72) Inventors: Giovanni Gozzini, Berkeley, CA (US); Gennadiy A. Agranov, San Jose, CA (US); Brian M. King, Saratoga, CA (US); Gershon Rosenblum, Fremont, CA (US); Mohammad Yeke Yazdandoost, San Jose, CA (US)

( * ) Notice: Subject to any disclaimer, the term of this patent is extended or adjusted under 35 U.S.C. 154(b) by 5 days.

(21) Appl. No.: 15/554,746

(22) PCT Filed: Mar. 24, 2016

(86) PCT No.: PCT/US2016/023891
§ 371 (c)(1),
(2) Date: Aug. 31, 2017

(87) PCT Pub. No.: WO2016/154378
PCT Pub. Date: Sep. 29, 2016

(65) Prior Publication Data
US 2018/0046837 A1 Feb. 15, 2018

Related U.S. Application Data

(60) Provisional application No. 62/138,107, filed on Mar. 25, 2015.

(51) Int. Cl.
*G06K 9/00* (2006.01)
*H04W 12/06* (2009.01)
(Continued)

(52) U.S. Cl.
CPC ......... *G06K 9/0004* (2013.01); *G01N 21/894* (2013.01); *G01N 21/956* (2013.01);
(Continued)

(58) Field of Classification Search
CPC ..... G06J 9/004; G01N 21/894; G01N 21/956; G01N 2021/95676; H04W 12/06; G06K 9/00046
See application file for complete search history.

(56) References Cited

U.S. PATENT DOCUMENTS 5,340,978 A   8/1994   Rostoker et al.
5,781,651 A   7/1998   Hsiao et al.
(Continued)

FOREIGN PATENT DOCUMENTS

CN   104035620 A   9/2014
CN   203838722 U   9/2014
(Continued)

OTHER PUBLICATIONS

Shen et al., "A Tetrahedron-Based Inhomogeneous Monte Carlo Optical Simulator," School of Biomedical Engineering and Sciences, Virginia Tech, Jan. 20, 2010, retrieved from the internet https://www.ncbi.nlm.nih.gov/pmc/articles/PMC2858330/, pp. 1-17.
(Continued)

*Primary Examiner* — Dominic J Bologna
(74) *Attorney, Agent, or Firm* — Allen, Dyer, Doppelt + Gilchrist, P.A.

(57) ABSTRACT

An electronic device may include an optical image sensor and a pin hole array mask layer above the optical image sensor. The electronic device may also include a display layer above the pin hole array mask layer that includes spaced apart display pixels, and a transparent cover layer above the display layer defining a finger placement surface capable of receiving a finger adjacent thereto.

30 Claims, 33 Drawing Sheets

(51) Int. Cl.
*G01N 21/894* (2006.01)
*G01N 21/956* (2006.01)
(52) U.S. Cl.
CPC .. *H04W 12/06* (2013.01); *G01N 2021/95676* (2013.01); *G06K 9/00046* (2013.01)

(56) References Cited

U.S. PATENT DOCUMENTS

| | | | |
|---|---|---|---|
| 5,937,557 | A | 8/1999 | Bowker et al. |
| 5,974,162 | A | 10/1999 | Metz et al. |
| 6,160,903 | A | 12/2000 | Hamid et al. |
| 6,288,779 | B1 | 9/2001 | Smith |
| 6,327,376 | B1 | 12/2001 | Harkin |
| 6,853,444 | B2 | 2/2005 | Haddad |
| 6,885,017 | B2 | 4/2005 | Lee et al. |
| 7,196,728 | B2 | 3/2007 | Campbell et al. |
| 7,489,391 | B2 | 2/2009 | Engheta et al. |
| 7,606,395 | B2 | 10/2009 | Hauke et al. |
| 8,406,487 | B2 | 3/2013 | Abramovich et al. |
| 8,805,033 | B2 | 8/2014 | Miesak et al. |
| 2004/0021786 | A1 | 2/2004 | Nakamura et al. |
| 2005/0128332 | A1 | 6/2005 | Tsuboi |
| 2008/0106629 | A1* | 5/2008 | Kurtz ............ H04N 7/144 348/333.01 |
| 2008/0123908 | A1 | 5/2008 | Waldman et al. |
| 2008/0232653 | A1 | 9/2008 | Rowe |
| 2008/0317303 | A1 | 12/2008 | Konno et al. |
| 2010/0067757 | A1 | 3/2010 | Arai et al. |
| 2011/0012793 | A1* | 1/2011 | Amm ............ H01Q 1/243 343/702 |
| 2012/0098746 | A1 | 4/2012 | Ogawa |
| 2012/0133618 | A1 | 5/2012 | Usukura et al. |
| 2012/0256089 | A1 | 10/2012 | Kanda et al. |
| 2013/0021289 | A1* | 1/2013 | Chen ............ G06F 1/1601 345/174 |
| 2013/0329031 | A1 | 12/2013 | Miura et al. |
| 2014/0192023 | A1 | 7/2014 | Hoffman |
| 2014/0355846 | A1 | 12/2014 | Lee et al. |
| 2016/0110025 | A1 | 4/2016 | Hossu |
| 2016/0224816 | A1* | 8/2016 | Smith ............ G02B 27/58 |
| 2017/0193270 | A1 | 7/2017 | Zhang |
| 2017/0249494 | A1* | 8/2017 | Zhang ............ G06K 9/00013 |

FOREIGN PATENT DOCUMENTS

| | | |
|---|---|---|
| CN | 104182727 | 12/2014 |
| CN | 204028936 U | 12/2014 |
| CN | 204142988 | 2/2015 |
| JP | 2000349959 | 12/2000 |
| JP | 2005339112 | 12/2005 |
| JP | 2009003821 | 1/2009 |
| JP | 2009225064 | 10/2009 |
| JP | 2010094499 | 4/2010 |
| JP | 2014075509 | 4/2014 |
| KR | 1020120013400 | 2/2012 |
| WO | 2008044781 | 4/2008 |
| WO | 2015140600 | 9/2015 |
| WO | 2015149545 | 10/2015 |
| WO | 2017132360 | 3/2017 |

OTHER PUBLICATIONS

Hiroshi Kano, "Non-Contact 3D Measurement Technologies and Light Field Camera—Relationship to Ranging for Auto Focus," The Journal of the Institute of Image Electronics Engineers of Japan, 2014, retrieved from the internet: https://www.jstage.jst.go.jp/article/iieej/43/4/43_612/article/-char/en, vol. 43, Issue 4, pp. 612-616.

* cited by examiner

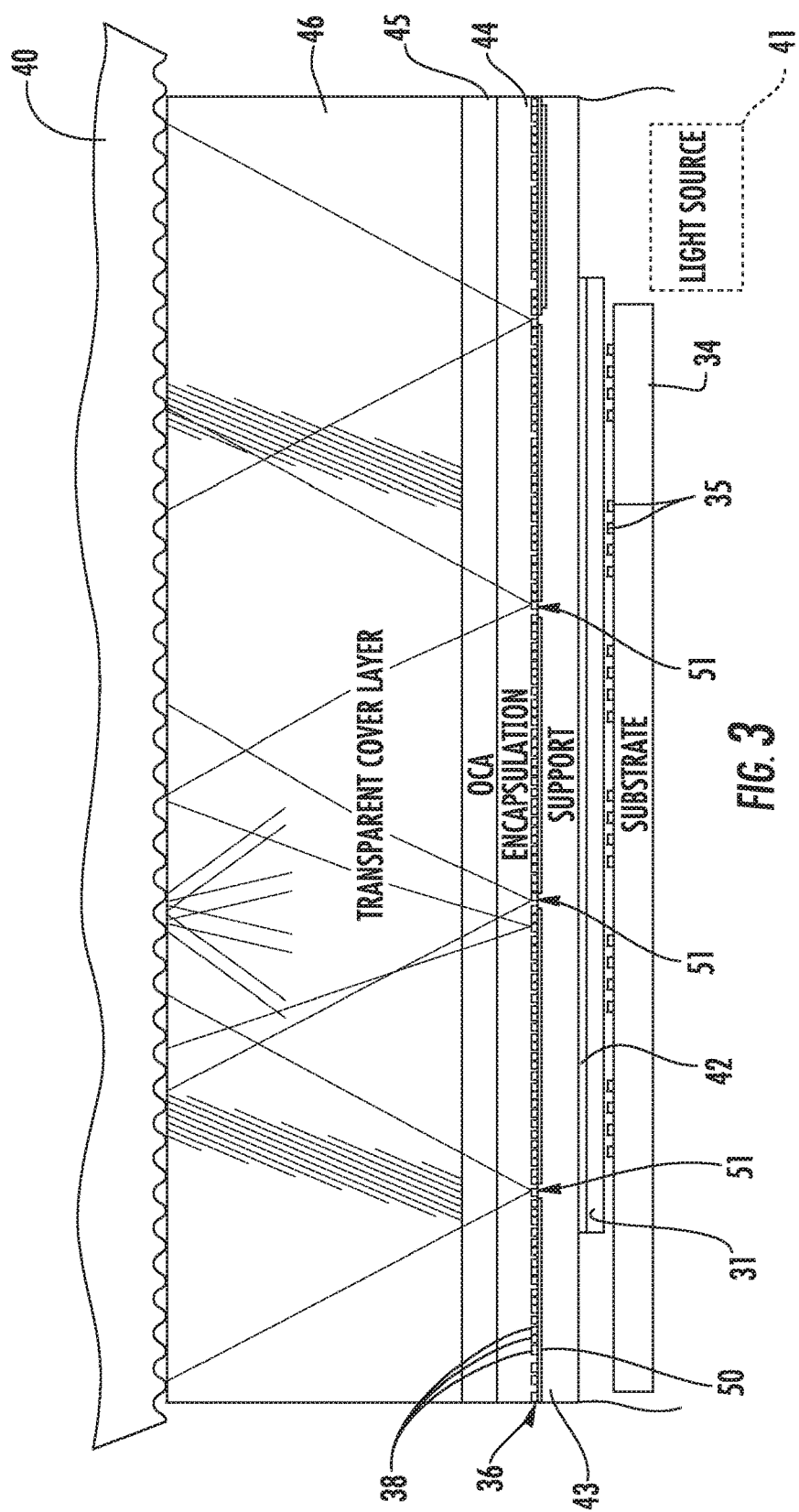

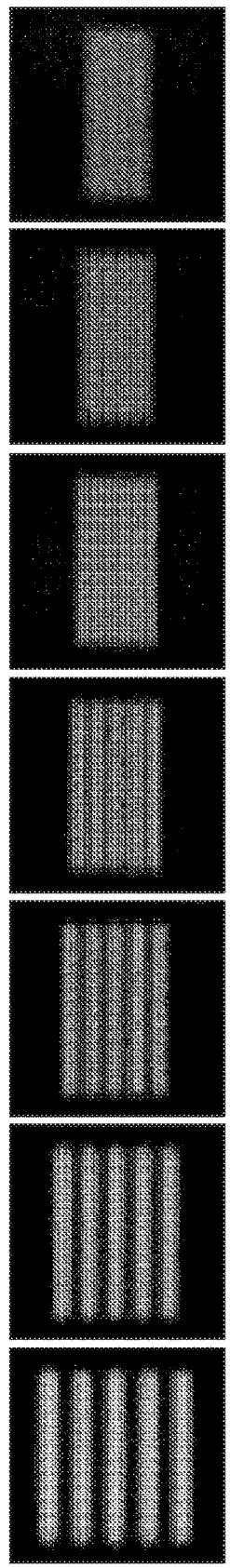

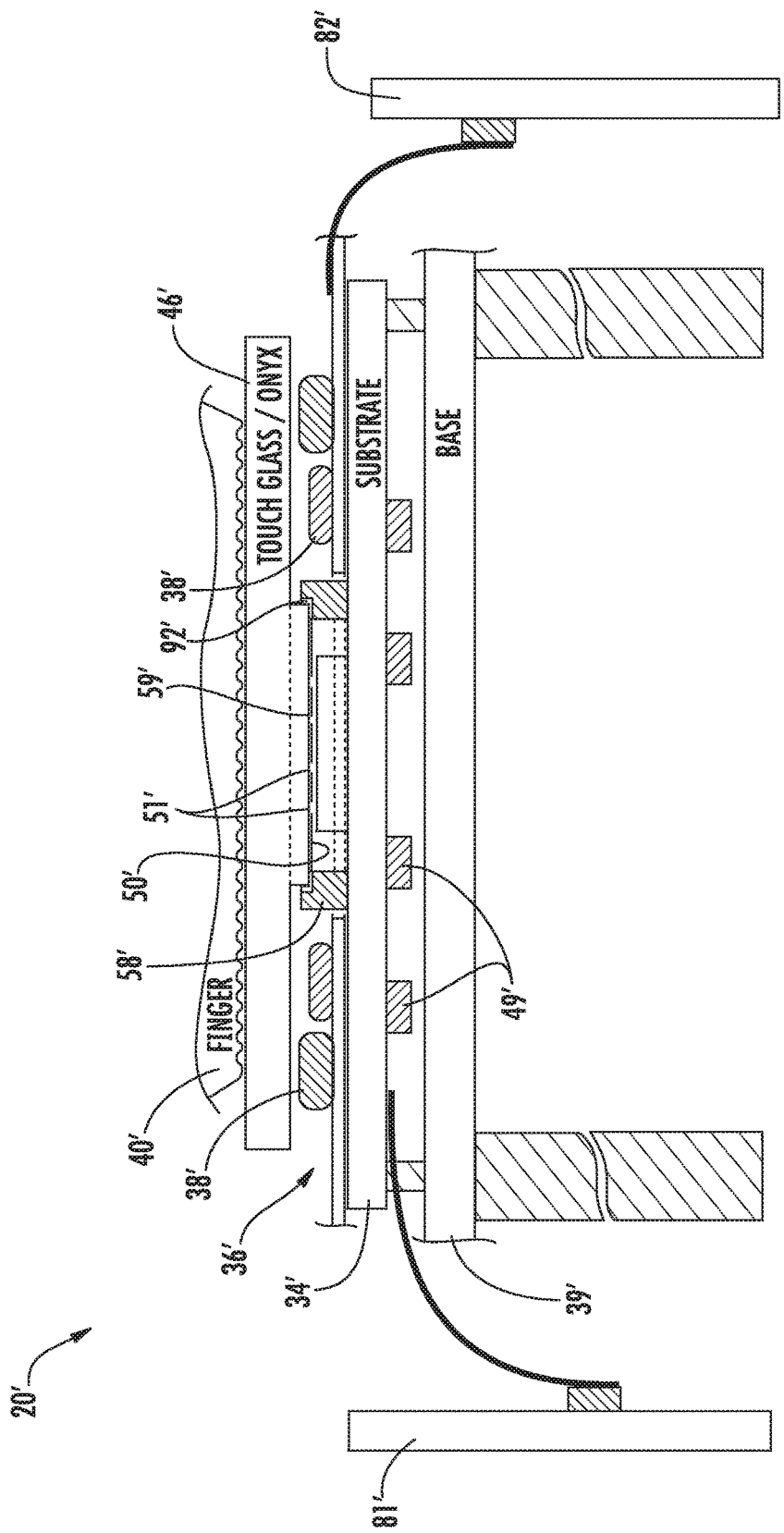

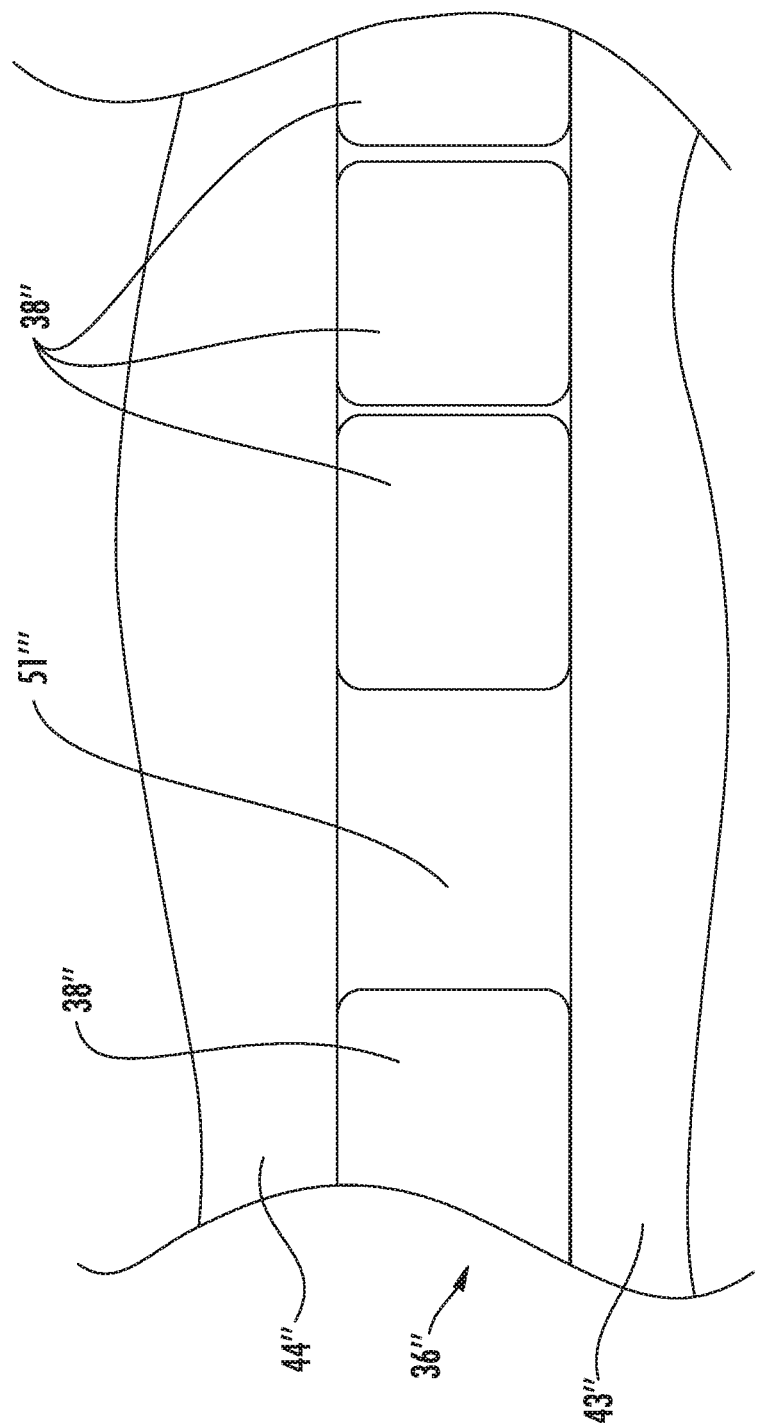

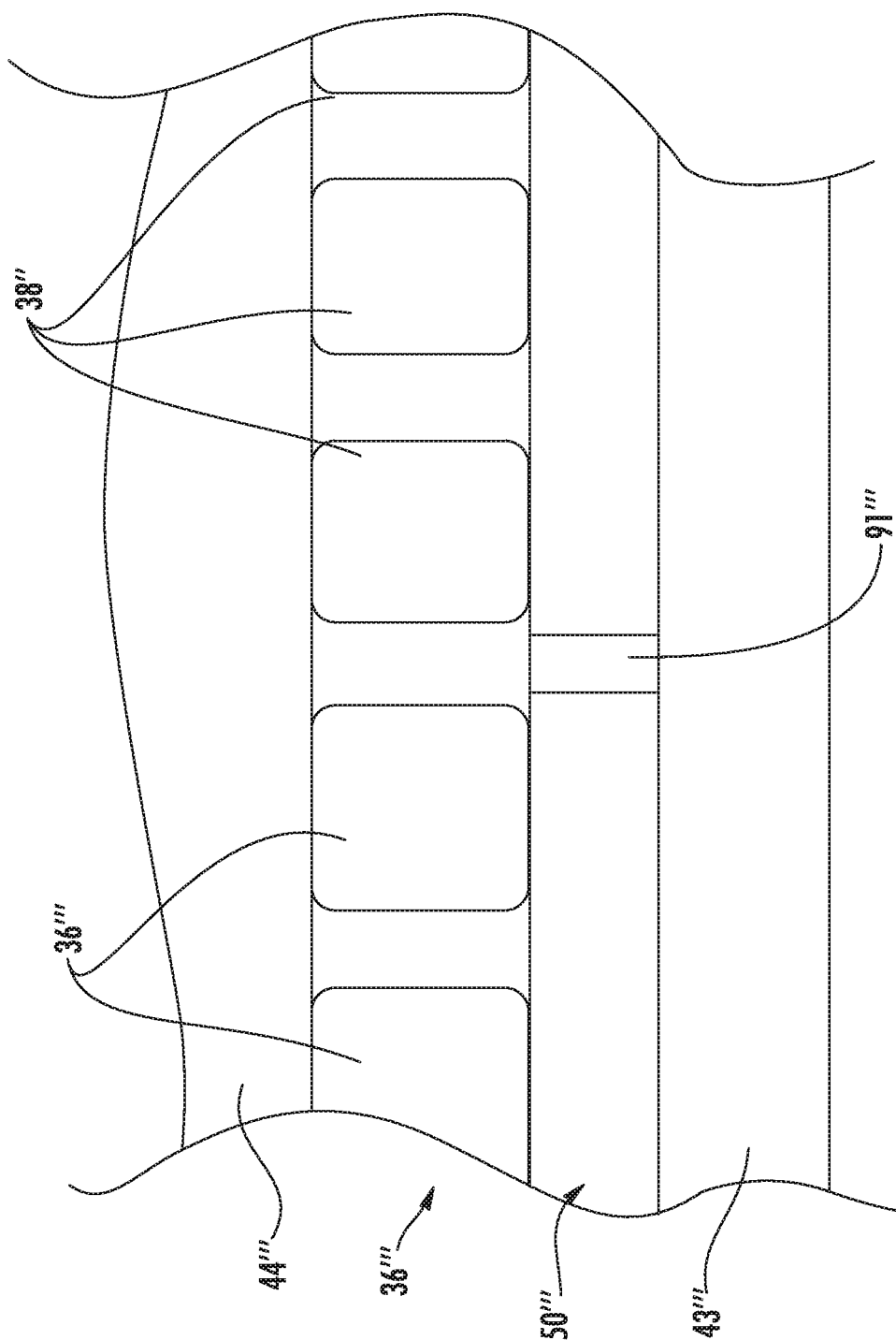

ELECTRONIC DEVICE INCLUDING PIN HOLE ARRAY MASK ABOVE OPTICAL IMAGE SENSOR AND RELATED METHODS

TECHNICAL FIELD

The present invention relates to the field of electronics, and, more particularly, to the field of optical image sensors.

BACKGROUND

Fingerprint sensing and matching is a reliable and widely used technique for personal identification or verification. In particular, a common approach to fingerprint identification involves scanning a sample fingerprint or an image thereof and storing the image and/or unique characteristics of the fingerprint image. The characteristics of a sample fingerprint may be compared to information for reference fingerprints already in a database to determine proper identification of a person, such as for verification purposes.

A fingerprint sensor may be particularly advantageous for verification and/or authentication in an electronic device, and more particularly, a portable device, for example. Such a fingerprint sensor may be carried by the housing of a portable electronic device, for example, and may be sized to sense a fingerprint from a single-finger.

Where a fingerprint sensor is integrated into an electronic device or host device, for example, as noted above, it may be desirable to more quickly perform authentication, particularly while performing another task or an application on the electronic device. In other words, in some instances it may be undesirable to have a user perform an authentication in a separate authentication step, for example switching between tasks to perform the authentication.

SUMMARY

An electronic device may include an optical image sensor and a pin hole array mask layer above the optical image sensor. The electronic device may also include a display layer above the pin hole array mask layer. The display layer includes a plurality of spaced apart display pixels. The electronic device may further include a transparent cover layer above the display layer defining a finger placement surface capable of receiving a finger adjacent thereto.

The electronic device may also include a light source capable of directing light into the finger when adjacent the transparent cover layer, for example. The optical image sensor, pin hole array mask layer, and finger placement surface may be configured to define overlapping areas at the finger placement surface, and spaced apart areas at the optical image sensor.

The pin hole array mask layer may have a plurality of openings each having a size in a range of 5-40 microns. The plurality of openings may be spaced from one another by a distance in a range of 1-3 millimeters, for example.

The pin hole array mask layer may be spaced from the optical image sensor by a distance in a range of 100-300 microns. The pin hole array mask layer may be spaced from the finger placement surface by a distance in a range of 1500-2000 microns, for example.

The pin hole array mask layer may include chromium, for example. The electronic device may also include a flexible circuit substrate carrying the optical image sensor. The optical image sensor may include an integrated circuit (IC) substrate and image sensing circuitry carried by the IC substrate.

The electronic device may also include an optically transparent body between the optical image sensor and the pin hole array mask layer. The electronic device may further include an optically clear adhesive layer above the optical image sensor, for example.

The optical image sensor may be capable of performing at least one of an authentication function, a spoof detection function, a navigation function, and a vital sign measurement function, for example. The optical image sensor may be capable of performing an authentication function based upon a fingerprint from the finger.

The display layer may include a touch display layer, for example. The pin hole array mask layer may have a plurality of spaced apart openings therein, and the pin hole array mask layer may include a plurality of lenses within the plurality of openings.

A method aspect is directed to a method of making an electronic device. The method includes positioning a pin hole array mask layer above an optical image sensor and positioning a display layer above the pin hole array mask layer. The display layer includes a plurality of spaced apart display pixels. The method also includes positioning a transparent cover layer above the display layer defining a finger placement surface capable of receiving a finger adjacent thereto.

BRIEF DESCRIPTION OF THE DRAWINGS

FIG. 3 is a schematic cross-sectional view of a portion of the electronic device of FIG. 1.

FIGS. 8a-8g are simulated images illustrating resolution of the optical image sensor for a given diameter of an opening in the pin hole array mask layer of the electronic device of FIG. 2.

FIG. 20 is a schematic cross-sectional view of a portion of an electronic device according to another embodiment of the present invention.

FIG. 21 is an enlarged schematic cross-sectional view of a portion of an electronic device according to another embodiment of the present invention.

FIG. 22 is an enlarged schematic cross-sectional view of a portion of an electronic device according to another embodiment of the present invention.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to refer to like elements in different embodiments.

Figure 1:
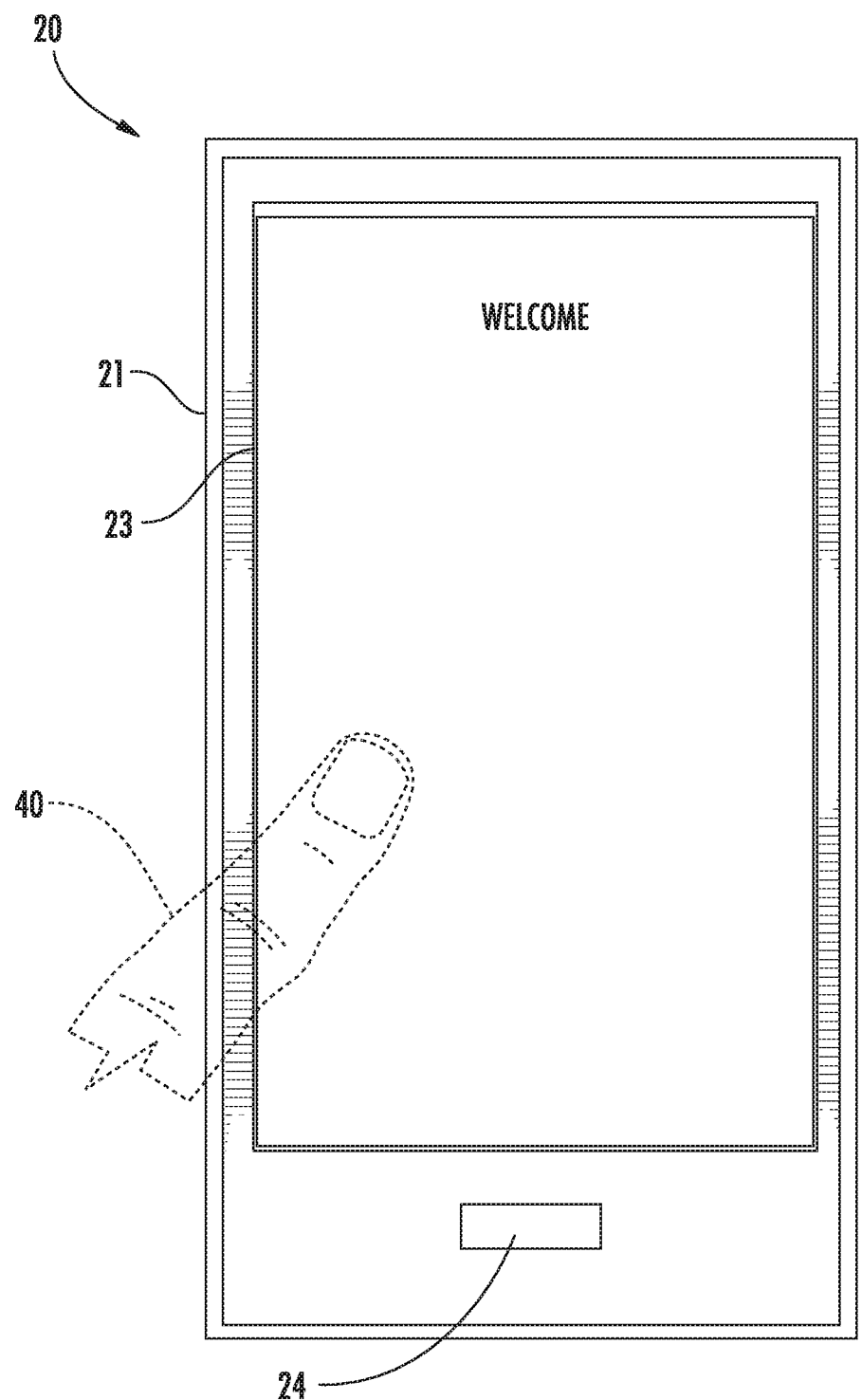
FIG. 1 is a plan view of an electronic device according to an embodiment.
Figure 2:
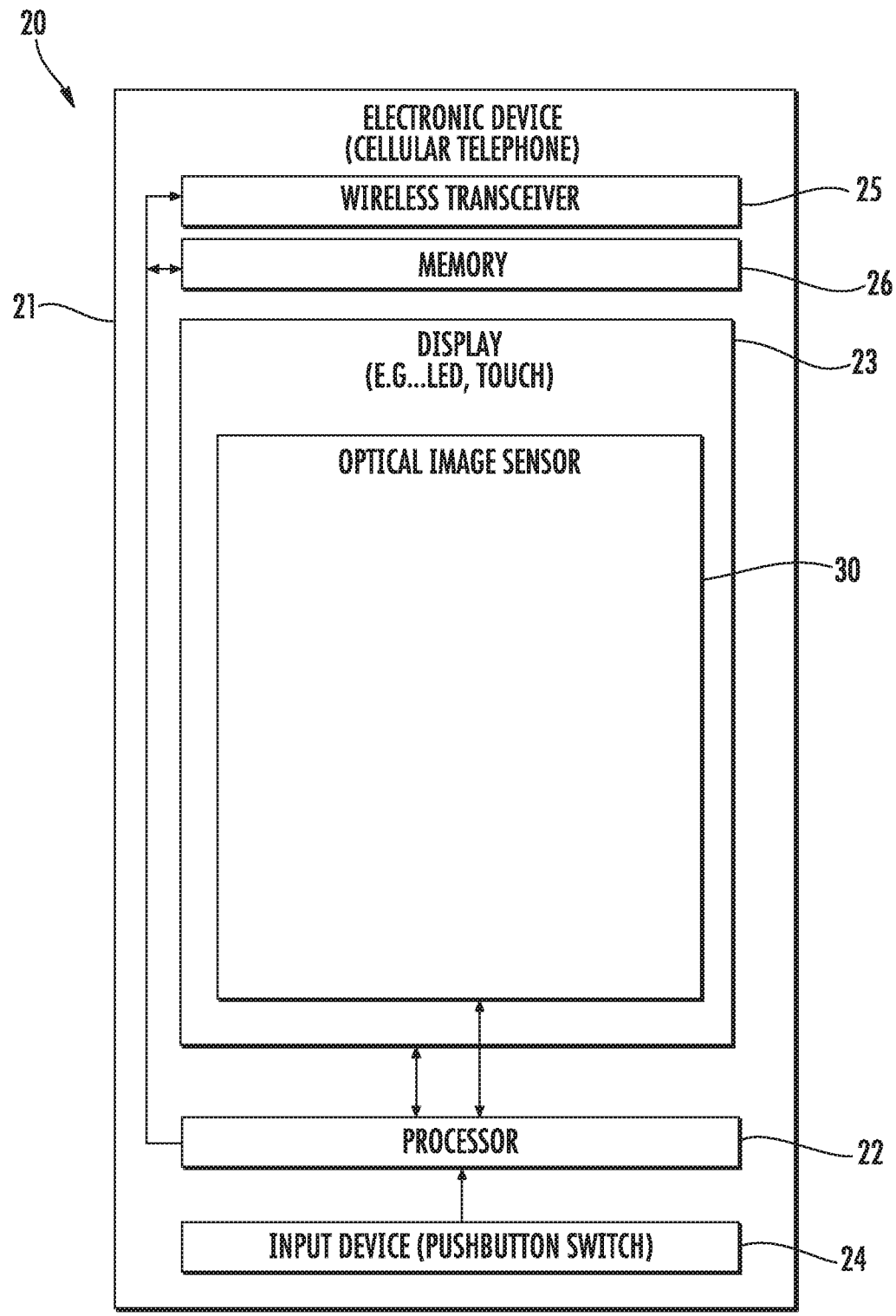
FIG. 2 is a schematic block diagram of an electronic device of FIG. 1.

Referring initially to FIGS. 1 and 2, an electronic device 20 illustratively includes a housing, for example, a portable housing 21, and a processor 22 carried by the portable housing. The electronic device 20 is illustratively a mobile wireless communications device, for example, a cellular telephone. The electronic device 20 may be another type of electronic device, for example, a tablet computer, laptop computer, wearable computer, etc.

A wireless transceiver 25 is also carried within the housing 21 and coupled to the processor 22. The wireless transceiver 25 cooperates with the processor 22 to perform at least one wireless communications function, for example, for voice and/or data. In some embodiments, the electronic device 20 may not include a wireless transceiver 25 or other wireless communications circuitry.

A display 23 is also carried by the portable housing 21 and is coupled to the processor 22. The display 23 may be a light emitting diode (LED) display, for example, and may have additional circuitry to provide touch display features, as will be appreciated by those skilled in the art. Further details of the display 23 are described below.

A memory 26 is also coupled to the processor 22. The memory 26 is for storing finger matching biometric template data, for example. The memory 26 may store other or additional types of data.

As will be appreciated by those skilled in the art, if the display 23 is in the form of a touch display, the touch display acts as both an input device and a display. As such, the display 23 would cooperate with the processor 22 to perform one or more device functions in response to input. For example, a device function may include a powering on or off of the electronic device 20, initiating communication via the wireless transceiver 25, and/or performing a menu function based upon input to the touch display.

More particularly, with respect to a menu function, the processor 22 may change the display 23 to show a menu of available applications based upon pressing or input to the touch display. Of course, other device functions may be performed based upon input to the touch display 23. Other or additional finger-operated user input devices may be carried by the portable housing 21, for example, a pushbutton switch 24, which may alternatively or additionally be used for device functions as will be appreciated by those skilled in the art.

Referring now additionally to FIG. 3, an optical image sensor 31 for sensing a biometric of a user, such as, for example, an image of the fingerprint patterns of the user's finger 40, is carried by the housing 21 under the display 23. More particularly, the optical image sensor 31 includes an integrated circuit (IC) substrate, and image sensing circuitry carried by the IC substrate. The optical image sensor 31 may be coupled to a circuit substrate, for example, a flexible substrate 34 by way of a grid array having ball grid array (BGA) contacts 35 or other coupling technique. The optical image sensor 31 may be a back-illuminated sensor or backside illumination (BSI) image sensor as will be appreciated by those skilled in the art.

The electronic device 20 optionally includes a light source 41. The light source 41 directs light into the user's finger 40, and may direct light for the optical image sensor 31. The light source 41 may be one or more light emitting diodes (LEDs) and/or may be part of the display layer 36. In other words, the display pixels 38 may be the light source or there may be a separate or additional light source. For example, different LEDs of the display may allow dynamic changing of and/or more flexibility with respect to the wavelengths of the light and the angle of illumination. A visible light source or invisible light source (e.g., infrared (IR) or ultraviolet (UV)), and/or another type of light source may be used, or a combination of light sources may be used. However, IR light may penetrate deeper within a user's finger 40, compared to other colors of light, for example, blue-colored light. It may be desirable that the light source 41 be synchronized with the optical image sensor 31, and more particularly, signal acquisition of the optical image sensor. For example, the light source 41 may cooperate with the optical image sensor 31 so that the optical image sensor operates in one or both of a rolling shutter mode and a global shutter mode, as will be appreciated by those skilled in the art. The global shutter mode may improve tolerance to background light or interference and reduce power consumption as will be appreciated by those skilled in the art. Additionally, the optical image sensor 31 may cooperate with a filter, for example, a narrow band spectral filter, that may correspond to the spectra of the light source 41. The filter may reduce background effects on finger recognition or increase tolerance to the background. The filter may be an optical filter, for example.

Further details of the rolling shutter and global shutter modes will now be described. A typical optical image sensor generally operates in a rolling shutter mode. In this mode, the integration time starts and ends at different times for each sensor line. Such operation may be inefficient when combined with active illumination, as it generally requires illumination to be turned in one of two regimes.

Figure 4A:
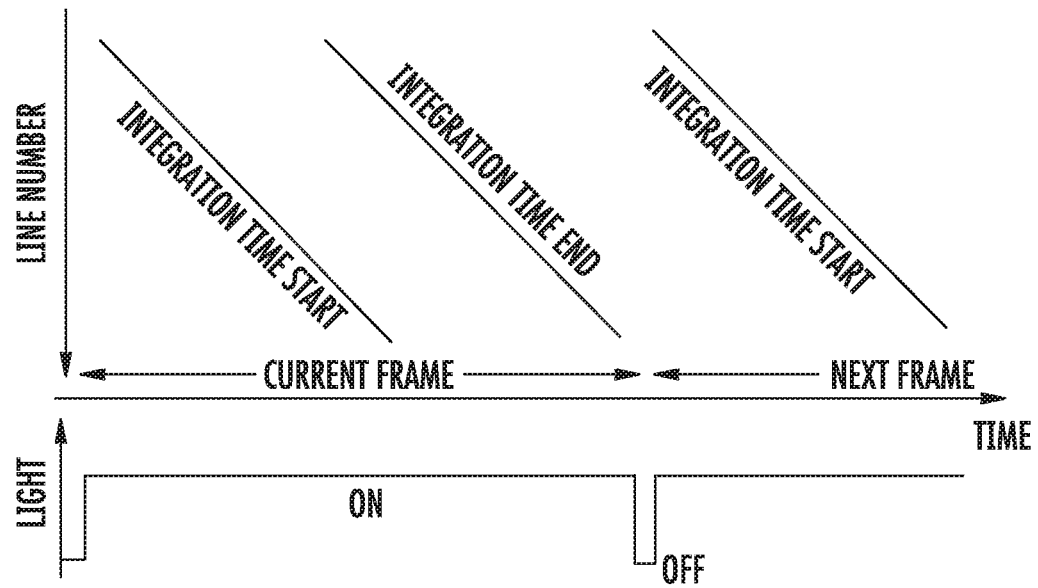
FIGS. 4a and 4b are graphs comparing light and integration line numbers relative to a frame according to rolling shutter techniques.

Referring now to the graph in FIG. 4a, in a first regime, illumination, i.e., the light source 41, is on from the start of the first line integration to the end of the last line integration. This regime has two disadvantages: 1) the integration time is shorter than the illumination on time, causing illumination power inefficiency; and 2) if the illumination switch is between the consecutive frames, such as to change the angle or wavelength, the next frame start is delayed until the first frame ends, adding a wait time no shorter than the readout time, causing a time inefficiency.

Figure 4B:
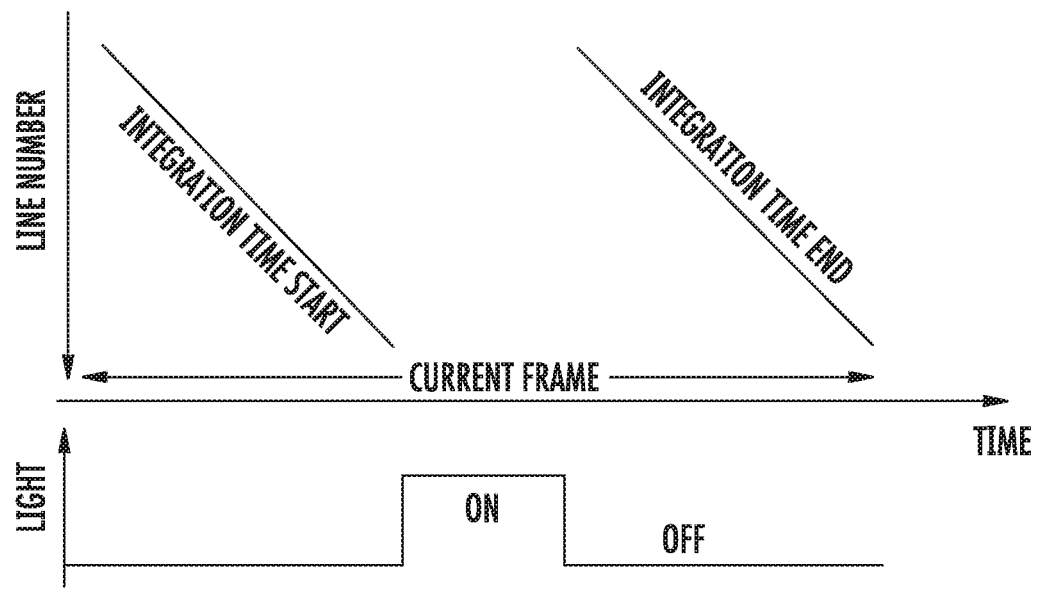

Referring now to the graph in FIG. 4b, in a second regime, the illumination is on from the start of the last line integration to the end of the first line integration. This regime has two disadvantages: 1) the integration time is longer than the illumination on time, causing background light interference inefficiency; and 2) the illumination duty cycle is relatively short causing a high peak power operation.

Figure 5:
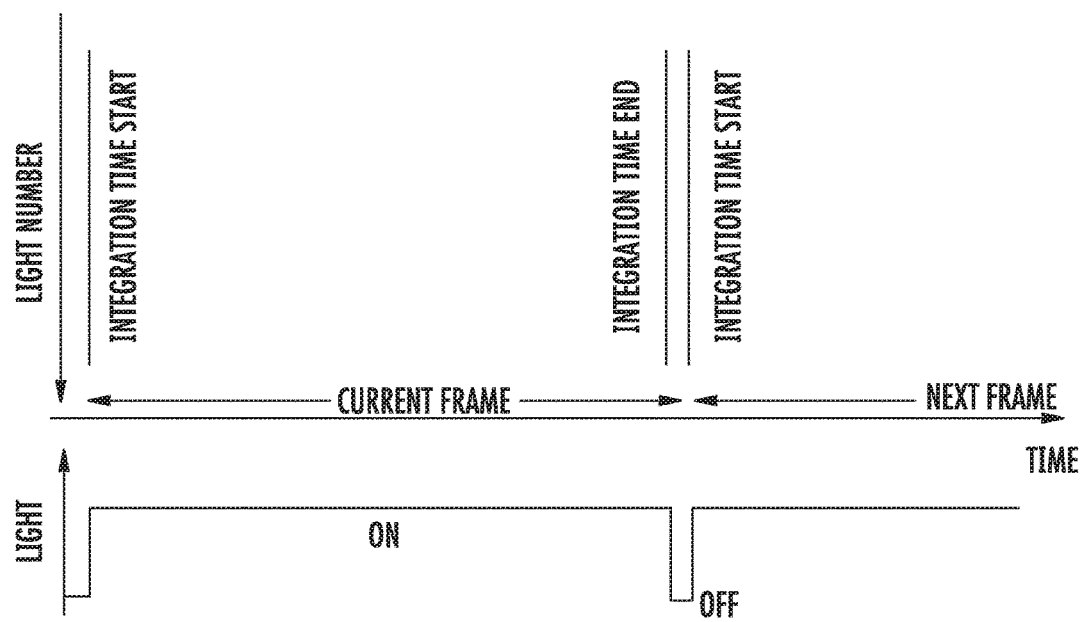
FIG. 5 is a graph comparing light to integration line number relative to a frame according to a global shutter mode.

Referring now to the graph in FIG. 5, it may be thus desirable to operate the optical image sensor 31 in a global shutter mode. In this mode the integration time starts and ends at the same time for all sensor lines. Such operation has three advantages: 1) The illumination on time is equal to the integration time causing efficient use of the illumination power; 2) there is typically no need to have dead time between the frames in case of illumination switching such as to change angle or wavelength; and 3) the illumination duty cycle is maximum, relaxing the need for high peak power operation.

An optically clear adhesive layer (OCA) 42 is above the optical image sensor 31, and more particularly, carried by an upper surface of the optical image sensor. An optically transparent body or support member 43 spaces the OCA layer 42 from a pin hole array mask layer 50. In other words, the support member 43 is between the OCA layer 42 and the pin hole array mask layer 50.

The pin hole array mask layer 50 is above the optical image sensor 31, for example, spaced from the optical image sensor by a distance in a range of 100-300 microns. More particularly, the pin hole array mask layer 50 is illustratively carried on a top surface of the support member 43. The pin hole array mask layer 50 is an opaque mask and has a plurality of openings 51 or pin holes therein to permit the passage of light therethrough. The openings 51 may be uniformly spaced or spaced in a honeycomb pattern, for example. The pitch of spacing of the openings 51 may be, for example, in a range of 1-3 mm and more particularly, about 1.5 mm. As will be appreciated by those skilled in the art, the spacing between the openings 51 or pitch affects image resolution. Additionally, each opening 51 may have a size in the range of 5-40 microns, for example. Of course, the size of each opening 51 or pin hole affects the sensed images from the optical image sensor 31, as will be described in further detail below. The pin hole array mask layer 50 is opaque, and thus does not permit light to pass through. The pin hole array mask layer 50 may include chromium, for example, a layer of chromium, to provide the opacity. Of course, other materials, whether in a layer or not, may be used to provide opacity.

A display layer 36, which is part of the display 23, is above the pin hole array mask layer 50. The display layer 36 illustratively includes an array of display pixels 38 and/or micro-lenses for displaying images, as will be appreciated by those skilled in the art. In particular, the display layer 36 may be part of a light-emitting diode (LED) display. The LEDs or display pixels 38 may be spaced apart to allow light to pass through, and may be aligned with the openings 51 or pin holes.

A display encapsulation layer 44 is over the display layer 36. Another optically clear adhesive layer 45 is over the display encapsulation layer 44. A transparent cover layer 46, for example, that includes onyx, is above the display layer 36 and defines a finger placement surface that is capable of receiving the user's finger adjacent thereto. More particularly, the transparent cover layer 46 is carried by the optically clear adhesive layer 45, and an upper surface of the transparent cover layer 46 defines the finger placement surface 47 for receiving the user's finger 40. The finger placement surface 47 may be spaced from the pin hole array mask layer 50 by a distance in a range of 1.5 mm-2 mm (i.e., 1500-2000 microns), for example. Of course, the finger placement surface 47 may be spaced from the pin hole array mask layer 50 by another distance, for example, based upon desired image characteristics.

In an exemplary electronic device 20 that includes the optical image sensor 31, the height of the layers may be as follows: the flexible substrate 34 may be about 0.15 mm thick, the optical image sensor 31 may be about 0.1 mm, the optically clear adhesive layer 42 may be about 0.05 mm, the support member 43 may be about 0.2 mm, the display encapsulation layer 44 may be about 0.1 mm, the second optically clear adhesive layer 45 may be about 0.15 mm, and the transparent cover layer 46 about 1.5 mm. Of course, the spacing between and size of each layer may be different, but as will be described below it may be desirable that the spacing between the optical image sensor 31 and the pin hole array mask layer 50 be relatively small.

The relative spacing and geometry of the optical image sensor 31, the pin hole array mask array layer 50, and the finger placement surface 47 define overlapping areas at the finger placement surface, and spaced apart areas at the optical image sensor. Accordingly, the spacing between the pin hole array mask layer 50 and the optical image sensor 31 determines an amount of sensed image overlap, i.e., at the finger placement surface 47. A larger spacing corresponds to a larger amount of image overlap which may be undesirable for processing. In other words, the more overlap, the more computationally intense image construction may be. In contrast, a smaller distance between the optical image sensor 31 and the pin hole array layer 50 may result in no significant overlap, and thus, images may be more easily reconstructed.

The optical image sensor 31, and more particularly, the image sensing circuitry senses a user's finger 40 or an object placed adjacent the finger placement surface 47, and based thereon, may perform one or more biometric functions, for example, user authentication (a matching operation), a biometric enrollment function, and/or a spoof detection function. Moreover, when the display 23 is in the form of a touch display, when the user contacts the touch display, for example, during a navigation function or other touch display input, data from the user's finger 40 is sensed or acquired by the optical image sensor 31, for example, for finger matching and/or spoof detection, as will be appreciated by those skilled in the art.

Operation of the electronic device 20 as it pertains to finger biometric sensing using the optical image sensor 31 will now be described. Light from the light source 41 and/or display pixels 38 is scattered based upon an object, for example, the user's finger 40, adjacent the finger placement surface 47 or on the transparent cover layer 46. The scattered light is captured by the optical image sensor 31 through the pin holes and/or micro-lenses in the display layer 36 and the openings 51 or pin holes in the pin hole array mask layer 50.

Advantageously, the display layer 36 is a multi-spectral and multi-shadow illuminator and generally not affected by ambient light. Moreover, in some embodiments, the display layer 36 may be used for spoof detection, for example, impedance based spoof detection and/or other light-based or electric field-based detection techniques, as will be appreciated by those skilled in the art.

Even still further, the die of the optical image sensor 31 has a relatively large amount of non-utilized areas, which can be allocated for other processing, for example, finger biometric or fingerprint processing and/or spoof detection, e.g. a spectrometer.

Using a pin hole array mask layer 50 as part of an imaging technique produces separate images of overlapping object areas. Shading and magnification of the image may be adjusted by adjusting different parameters with respect to size and distance from object to the pin hole array layer 50 and to the optical image sensor 31. For example, a magnification of 0.114 can be achieved based upon the height and the average refractive index ratio. Opening or pin hole image shading is given by a $\cos^4$ function. Shading allows for separation of the sensed images, even though there are overlapping areas. Moreover, the shading determines the effective size of the object area images by a single opening 51 or pin hole.

With respect to image overlap, using a signal level in the range of 64%-100%, a field-of-view angle of ±26.5° may be obtained. When used with an opening 51 or pin hole size of 200 microns, an object area size of 1750 microns, and a spacing or pitch of the openings of 1500 microns, the object may be full covered by the imaged areas. By using a signal level in the range of 20%-100%, a field-of-view angle of ±48° may be obtained. When used with an opening 51 or pin hole size of 200 microns, an object area size of 1750 microns, and a pin hole spacing or pitch of the openings of 1500 microns, each object area is sensed or imaged multiple times from different angles in the same capture. The overlap information may be used to improve resolution and signal-to-noise ratio (SNR), and/or extract 3D information, for example.

With respect to resolution, the use of the pin hole array layer 50 allows image resolution of about 15 microns. Thus, a relatively wide range of pixel sizes may be used. For example, an object plane resolution of about 120 microns may be achieved.

More particularly, the pin hole optical system resolution may be determined based upon a pin hole imaging point spread function (PSF) that is a convolution of geometrical and diffraction PSF. Both are axially symmetric 2D functions. The geometrical PSF quantifies blurring due to the finite size of each opening or pin hole. The geometrical PSF is given by the pin hole circle projections onto the optical image sensor 31 (for image space resolution) or onto the object (for object space resolution). The diffraction PSF quantifies the additional blurring due to the light diffraction off small openings, for example, for a circular aperture, it is given by the first Bessel function.

Figure 6A:
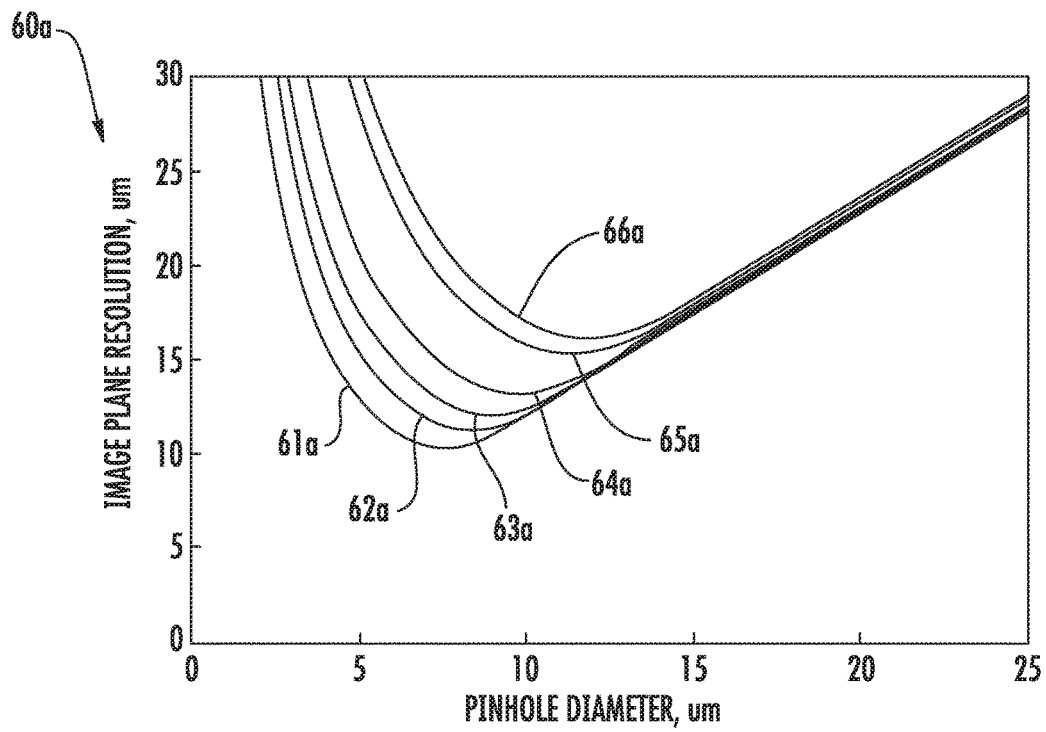
FIGS. 6a and 6b are graphs of estimated image and object plane resolution respectively for the optical image sensor of the electronic device of FIG. 1.
Figure 6B:
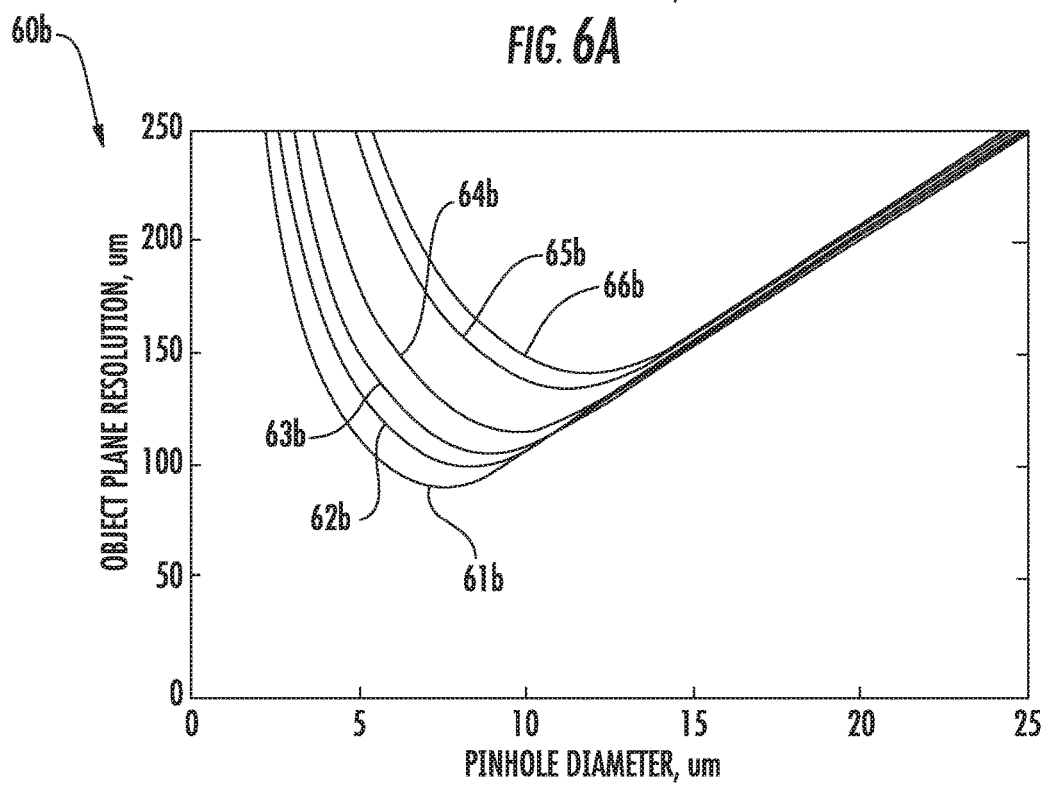

Referring to FIGS. 6a and 6b, the graphs 60a and 60b are graphs of opening 51 or pin hole size based upon an object-to-opening distance of 1750 microns and an optical image sensor-to-opening distance of 200 microns. The graphs 60a, 60b plot the diameter of each opening 51 in microns against the image plane resolution (FIG. 6a) and the object plane resolution (FIG. 6b) in microns, respectively. Lines 61a, 61b correspond to light having a wavelength of 380 nm, lines 62a, 62b correspond to light having a wavelength of 460 nm, lines 63a, 63b correspond to light having a wavelength of 525 nm, lines 64a, 64b correspond to light having a wavelength of 630 nm, lines 65a, 65b correspond to light having a wavelength of 850 nm, and lines 66a, 66b correspond to light having a wavelength of 940 nm. The size of the openings 51 that may be particularly well suited for visible light is 9 microns.

Additionally, the lines' PSF width rise at relatively large pin holes or openings 51 is the geometric resolution-dominant regime. The fast PSF width rise at relatively smaller openings 51 is the diffraction-dominant regime. The two effects combined produce what may be considered an optimum pin hole size for the best resolution. It may be desirable that the selection of the openings 51 size be somewhat above the optimum determined resolution, for example, to trade-off resolution for signal-to-noise ratio (SNR).

Figure 7A:
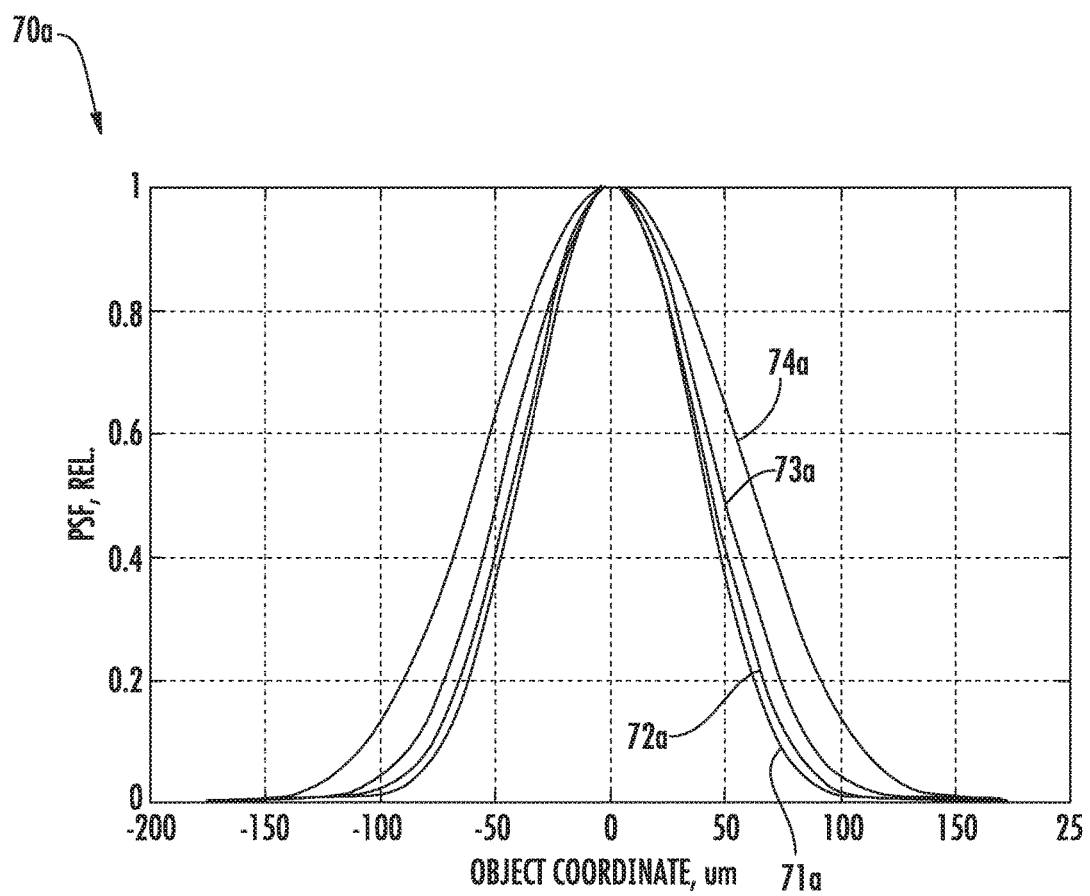
FIGS. 7a and 7b are graphs of estimated imaging resolution in terms of point-spread function shape for the optical image sensor of the electronic device of FIG. 1.
Figure 7B:
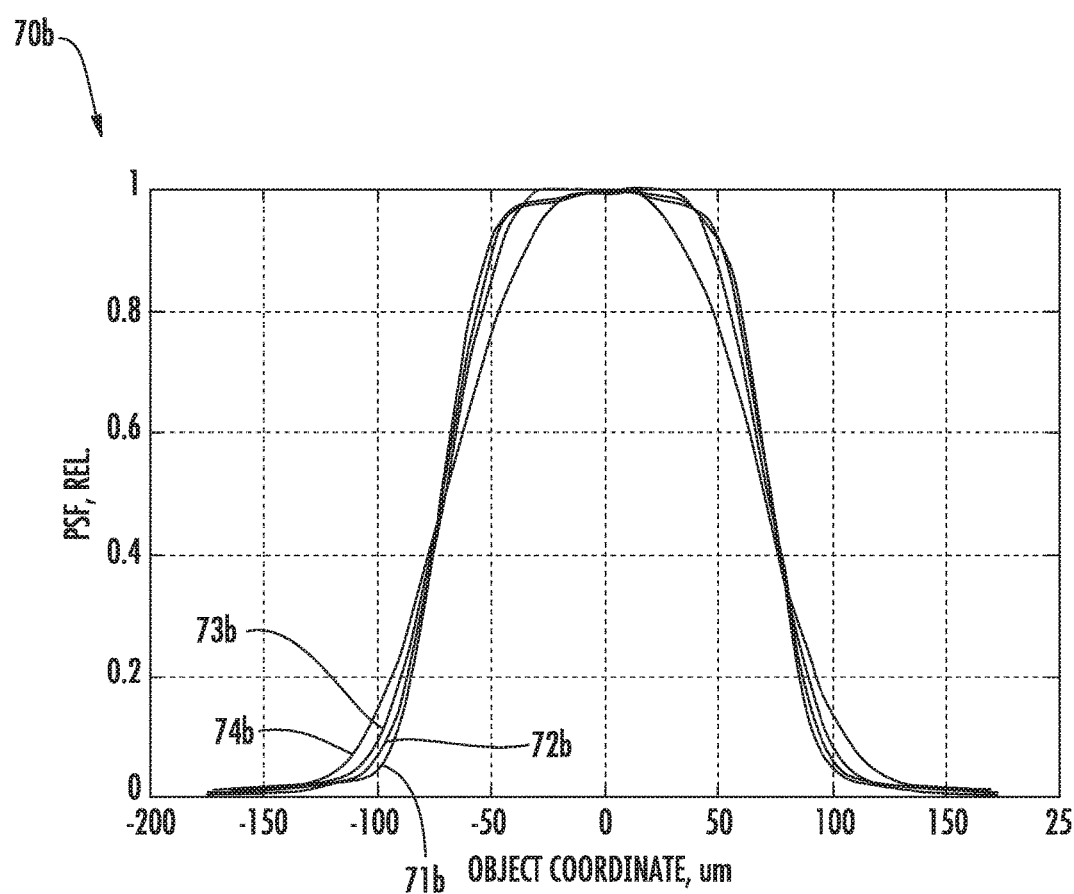

Referring now to the graphs 70a, 70b in FIGS. 7a and 7b, pin hole imaging resolution is illustrated. The graph 70a in FIG. 7a corresponds to an opening 51 or pin hole size of 9 microns, an object-to-opening distance of 1750 microns, and an image sensor-to-opening distance of 200 microns, while the graph 70b in FIG. 7b corresponds to an opening or pin hole size of 15 microns, an object-to-opening distance of 1750 microns and an image sensor-to-opening distance of 200 microns. Lines 71a, 71b correspond to light having a wavelength of 460 nm, lines 72a, 72b correspond to light having a wavelength of 525 nm, lines 73a, 73b correspond to light having a wavelength of 630 nm, and lines 74a, 74b correspond to light having a wavelength of 850 nm. Illustratively, for an opening 51 or pin hole diameter of 9 microns, the object plane resolution (1/e) is 105 microns, while for an opening 51 or pin hole diameter of 15 microns, the object plane resolution (1/e) is 155 microns. The graph 70a corresponds to a relatively small pin hole size, a diffraction regime, has a bell shape, and thus, a relatively significant wavelength dependence. The graph 70b corresponds to a relatively large pin hole size, a mostly geometrical regime, has a square shape, and thus negligible wavelength dependence.

It is also desirable to account for pixel blurring. The pixel PSF is a convolution of pixelization and crosstalk PSF. The pixelization PSF is due to the finite size of the pixel, and it can be modeled by a 2D-square sinc function or by integrating a super-sampled image.

The crosstalk PSF is the pixel property that is measured, for example, by way of angle and wavelength. The crosstalk PSF depends on the incoming angle, and more particularly, on pixel position with respect to the image center. The crosstalk PSF typically is of the order of one pixel in size, but can have a long-range tail, especially for near infrared (NIR) light, for example. Pixel blurring, however, is not generally expected to be relatively significant compared to optical blurring since the pixel size is significantly smaller than the size of the openings 51 or pin holes.

Referring now to FIGS. 8a-8g, simulated images illustrating exemplary resolutions are illustrated. The images are for green light, an opening 51 diameter of 15 microns, and a resolution of 155 microns. FIG. 8A illustrates 4 lines per millimeter with a line width of 125 microns. FIG. 8B illustrates 5 lines per millimeter with a line width of 100 microns. FIG. 8C illustrates 6 lines per millimeter with a line width of 83 microns. FIG. 8D illustrates 7 lines per millimeter with a line width of 71 microns. FIG. 8E illustrates 8 lines per millimeter with a line width of 63 microns. FIG. 8F illustrates 9 lines per millimeter with a line width of 56 microns, and FIG. 8G illustrates 10 lines per millimeter with a line width of 50 microns. A 1/e resolution of 155 microns advantageously allows for resolving of up to about 7 lines per millimeter, which may depend on a contrast degradation limit, for example.

With respect to shading, shading includes both optical shading and pixel shading. Optical shading can be approximated by the "cosine-4$^{th}$" geometrical factor. Light is received at the optical image sensor 31 at angles that depends on the refractive index ratio of the pin hole plane. The pixel shading is measured and is expected to be no more than an extra cosine factor in addition to the geometrical effect.

With respect to signal-to-noise ratio (SNR) and integration time, the size of each opening 51 or pin hole drives the resolution-SNR trade off. The signal level is based upon pin hole plane irradiance, opening 51 or pin hole size, pixel sensitivity, integration time, and shading. The noise level for a given optical image sensor may be a function of the signal with constant parameters including pixel properties, such as for example, read noise, photo response non-uniformity (PRNU), and fixed pattern noise (FPN).

For example, for a resolution-optimal opening diameter of 9 microns, the F-number is 22.2. For an opening diameter of 15 microns, with a sensor distance of 200 microns, the F-number is 13.3 (a resolution loss of about 1.5×, and an integration time reduction for the same SNR of about 2.8×). As will be appreciated by those skilled in the art, the image center signal is given by:

Signal=luminance[cd/m$^2$]
\*π\*reflectivity\*transmissivity/(4$F^2$)\*sensitivity
[e/lx–s]\*tau[s]

For a typical display luminance of about 520 cd/m$^2$, reflectivity of about 70%, F/13.3, pixel pitch 6 microns, integration time of 100 ms, the resultant signal may be about 140e, with an SNR of about 11. This SNR may be considered relatively low, and thus it may be desirable for the image modulation to be about 10% for a workable contrast. A larger effective pixel pitch, i.e., spacing between pixels, for example via binning, may be considered for an SNR increase or an integration time decrease.

With respect to image distortion, image distortion may result based upon a fisheye or inverse-fisheye effect. The image distortion may be due to the difference in the refractive index between the object interface media and the optical image sensor 31, for example, and is modeled by the sine ratio refraction function. Pin hole imaging itself does not introduce significant distortion, thus maintaining the angle tangents relatively constant. Distortion may be reduced by using materials having a closer match, for example nearly the same refractive index. Distortion may be corrected by image processing before stitching together individual images, as will be appreciated by those skilled in the art.

Figure 9:
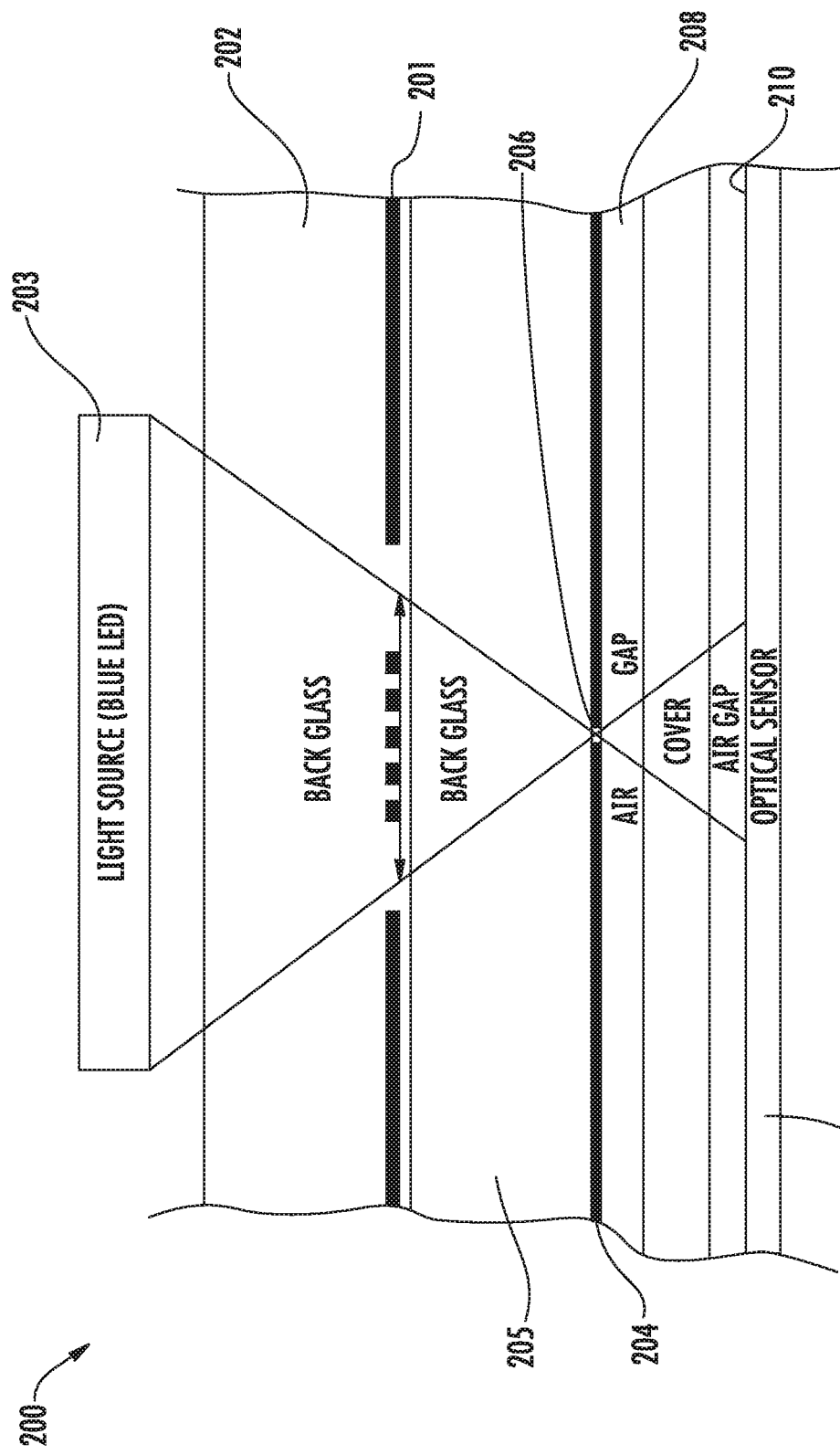
FIG. 9 is a schematic cross-sectional view of a prototype electronic device for generating images according to the optical image sensing principles of the electronic device of FIG. 1.
Figure 10D:
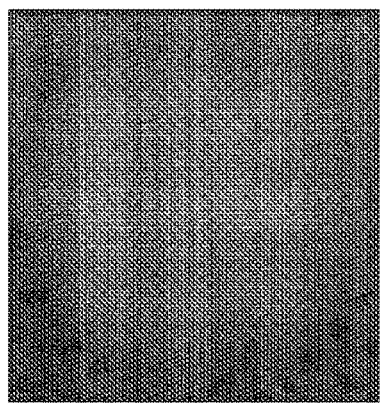
FIGS. 10a-10h are images captured using the prototype electronic device of FIG. 9 illustrating image resolution.
Figure 10C:
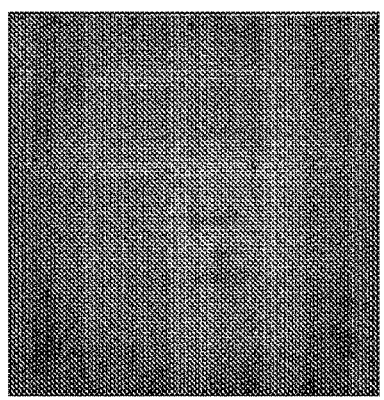
Figure 10B:
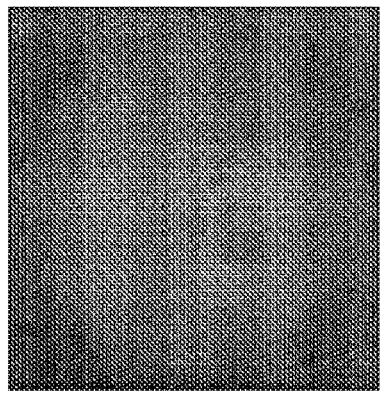
Figure 10A:
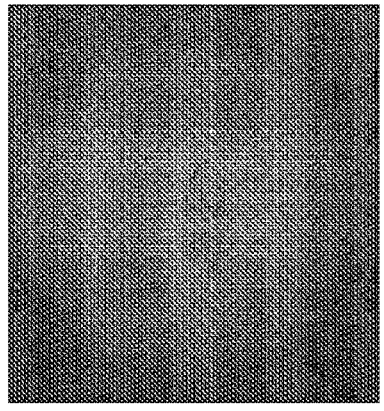
Figure 10E:
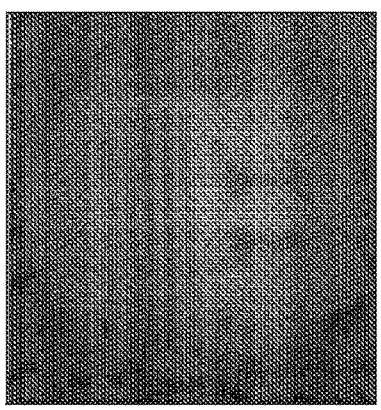
Figure 10F:
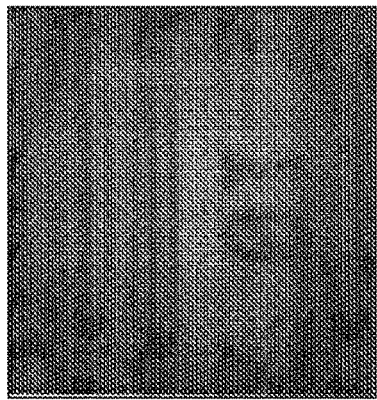
Figure 10G:
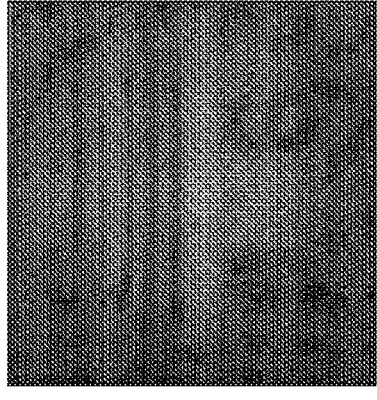
Figure 10H:
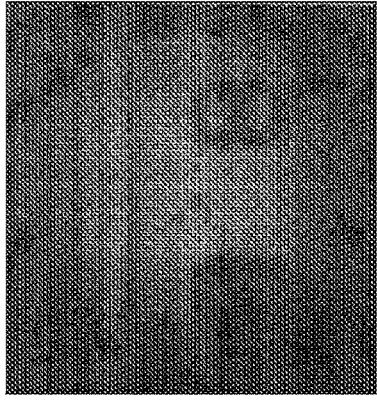
Figure 11A:
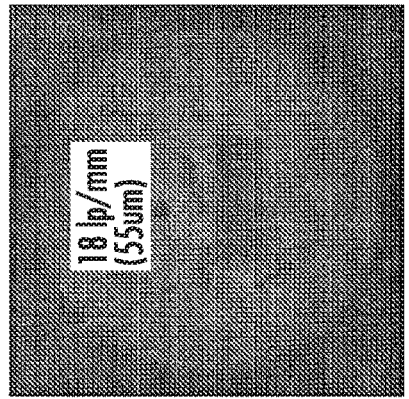
FIGS. 11a-11h are simulated images using the prototype electronic device of FIG. 9 illustrating image resolution.
Figure 11B:
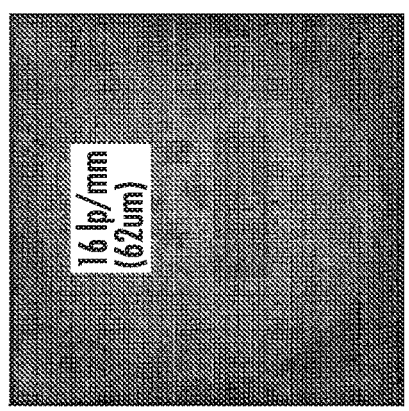
Figure 11C:
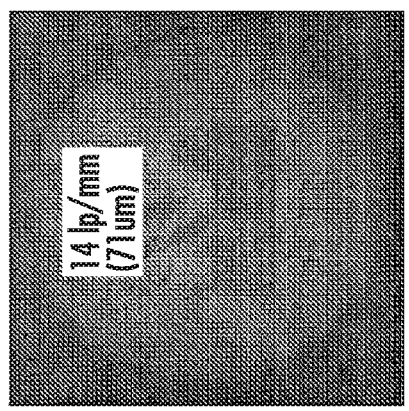
Figure 11D:
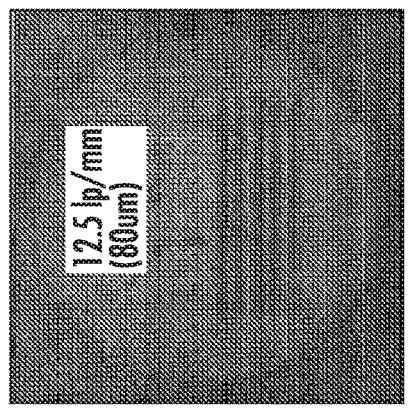
Figure 11E:
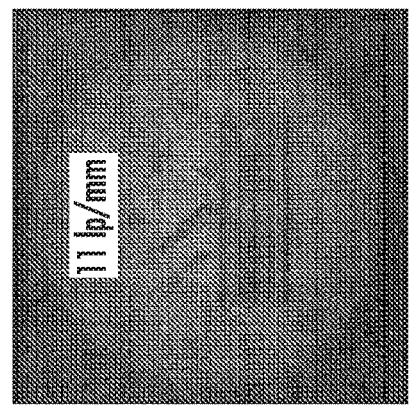
Figure 11F:
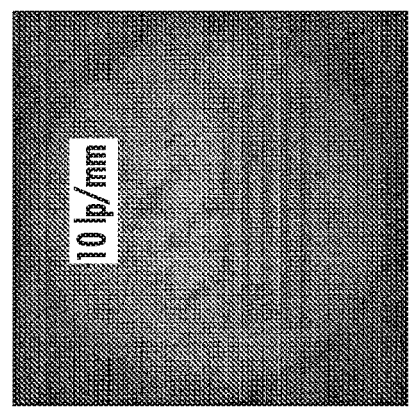
Figure 11G:
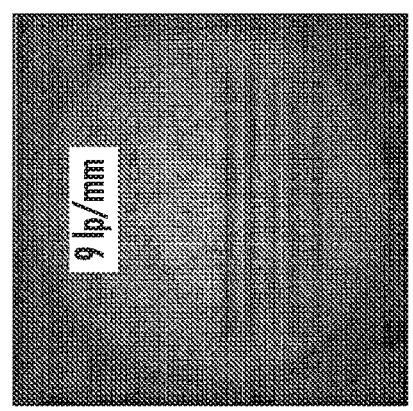
Figure 11H:
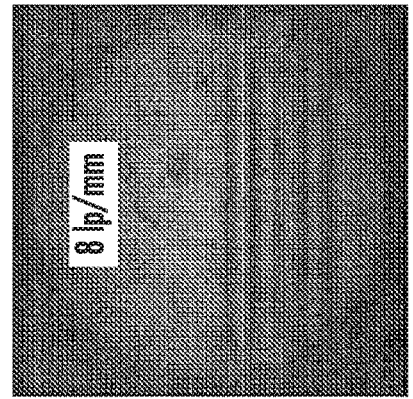

Referring now to FIG. 9, a prototype electronic device 200 was used to generate images according to the principles described above. More particularly, a chromium mask 201 having a thickness of about 12 microns carried by a back glass 202 having a refractive index of 1.5 and a thickness of 1500 microns was used to simulate an object to be sensed. The chromium mask 201 simulating the object was a Thorlabs R2L2S1P positive resolution target having a 2-inch by 2-inch size, a soda lime glass substrate (back glass) and a chromium pattern.

A diffused light source 203 was positioned above the chromium mask 201. The diffused light source 203 included multiple blue light-emitting diodes (LEDs) uniformly illuminating a diffuser over 2 inches. The central wavelength was about 450 nm. The light source 203 was limited to blue LEDs because of a residual transmission of chromium masks at higher wavelengths that caused reduced contrast.

The chromium mask 201 was spaced from a pin hole array mask layer 204 by about 1500 microns as the pin hole array mask layer was also carried by a back glass 205 having a refractive index of about 1.5 and a thickness of about 1500 microns. The pin hole array mask layer 204 had a thickness of about 12 microns, and the diameter of the single opening 206 in the pin hole array mask layer was 12 microns.

An optical image sensor 207 was below the pin hole array mask layer 204 and spaced therefrom by about 750 microns with an associated refractive index of about 1.3. The 750 micron spacing included a 150 micron air gap 208, a cover glass layer 209 with a thickness of 300 microns and a refractive index of 1.5, and a second air gap 210 having a thickness of 300 microns. The predicted object plane resolution was 38 microns (PSF–1/e diameter; equivalent to a minimum resolved line-pair width).

Referring additionally to the images in FIGS. 10A-10H and FIGS. 11A-11H, the prototype was used to generate images, which were compared to simulated images, respectively. FIGS. 10A-10H correspond to captured or generated images for 18, 16, 14, 12.5, 11, 10, 9, and 8 lines per millimeter, respectively. FIGS. 11A-11H correspond to the simulated images for 18, 16, 14, 12.5, 11, 10, 9, and 8 lines per millimeter, respectively. It should be noted that 18 lines per millimeter is still resolved, but as illustrated, the contrast is relatively low (line width of 28 microns). Referring particularly to FIGS. 10E-10H, the visible distortion is due to the "inverse fisheye" effect to the refraction index step on the pin hole or opening 51.

Figure 12A:
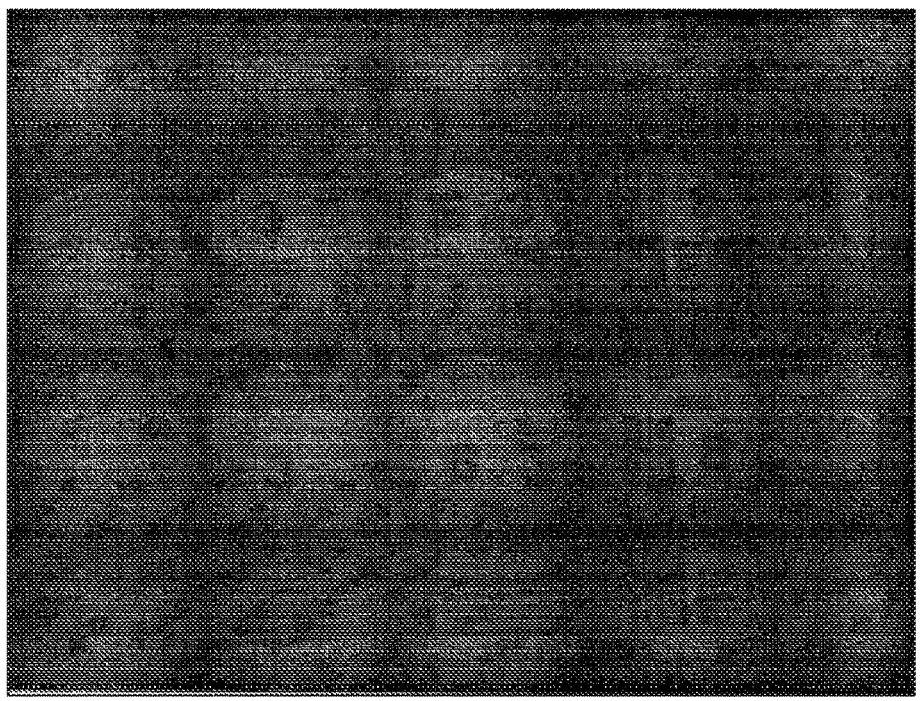
FIGS. 12a-12c are examples of separate sub-images of overlapping object areas from the prototype electronic device of FIG. 9.
Figure 12B:
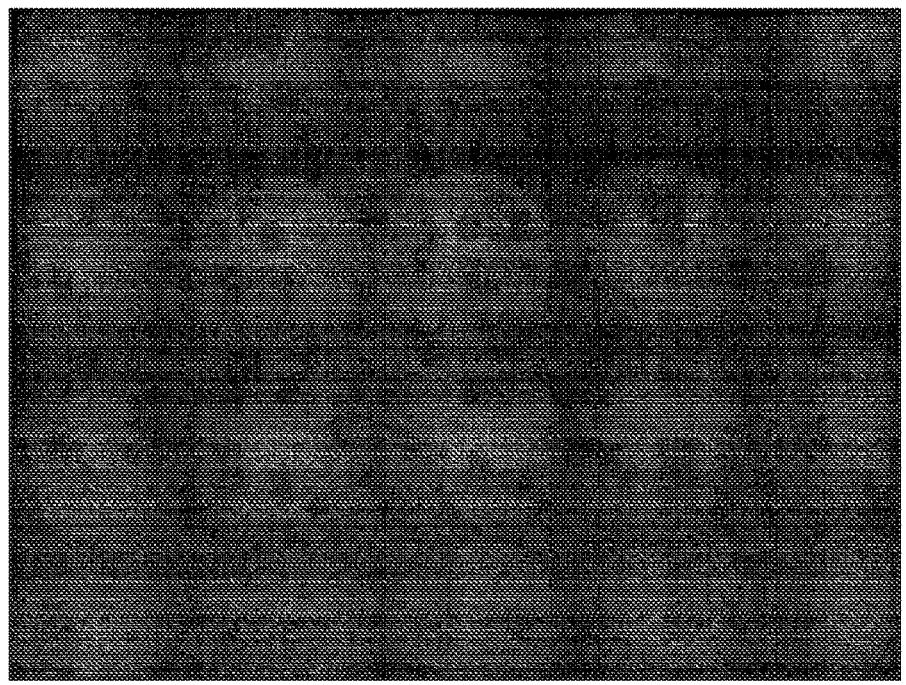
Figure 12C:
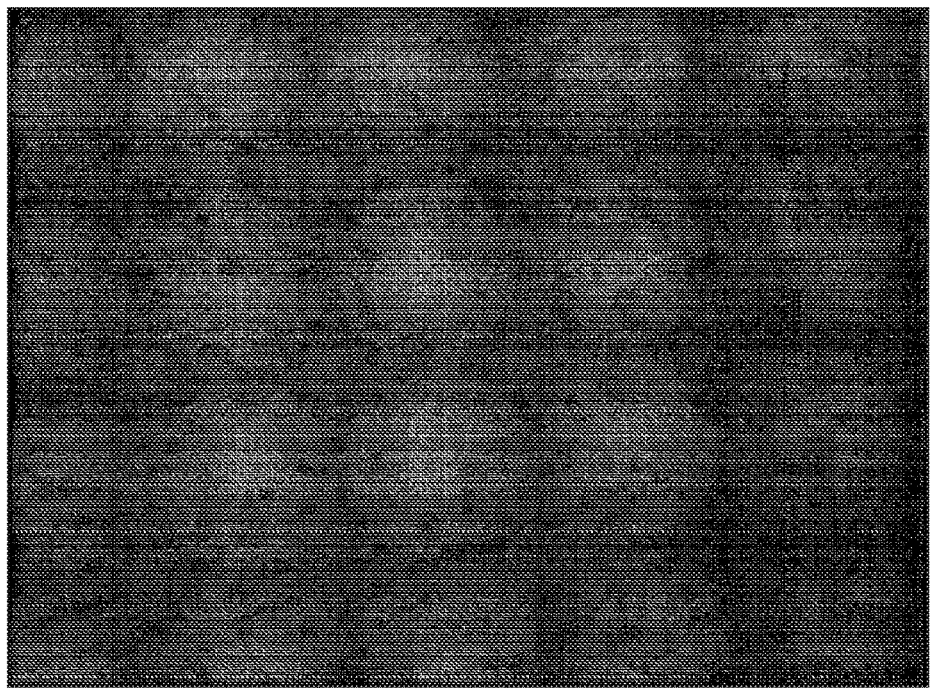
Figure 13A:
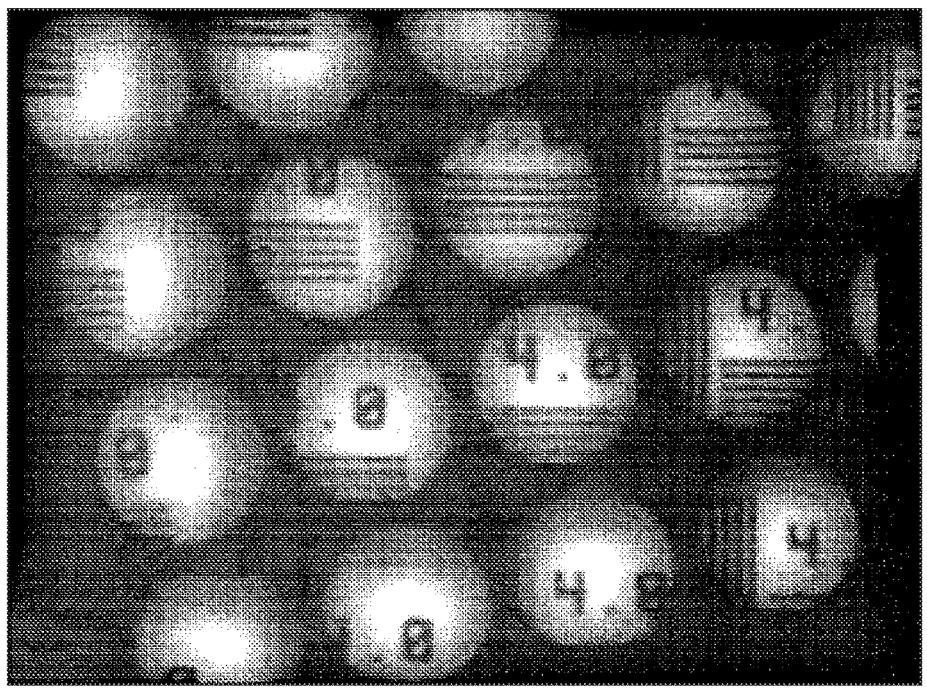
FIGS. 13a-13b are captured images illustrating restoral of a single image from overlapping sub-images from the prototype electronic device of FIG. 9.
Figure 13B:
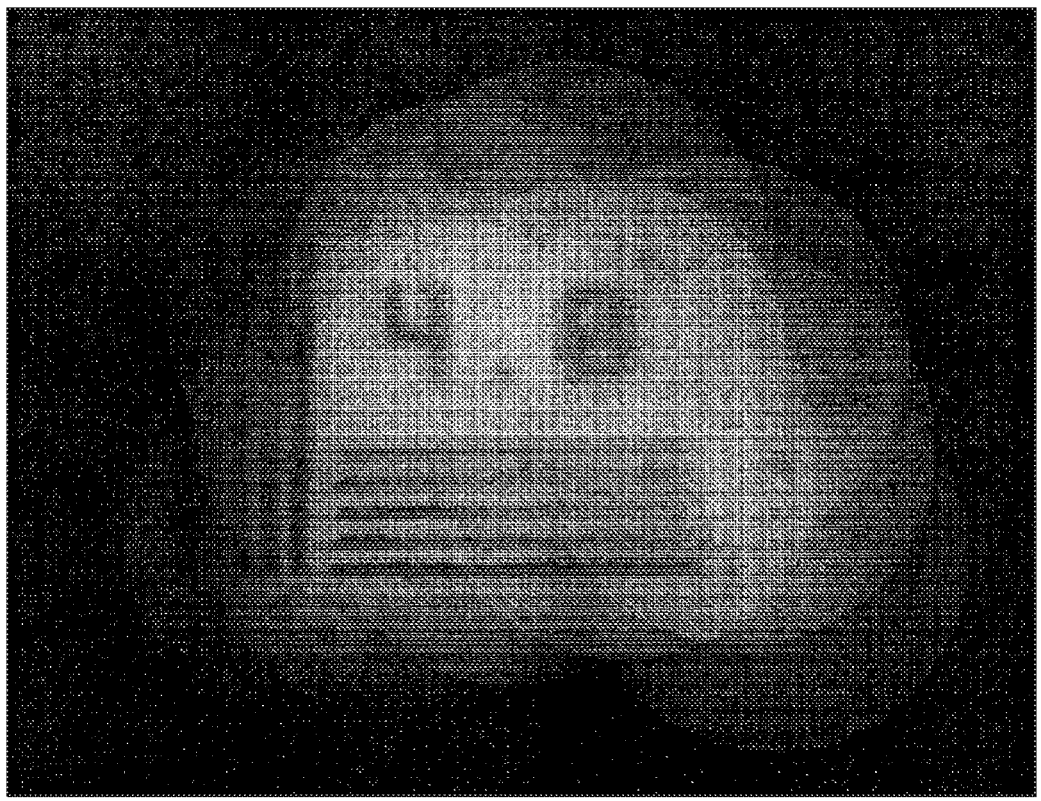

Referring now to FIGS. 12A-12C, exemplary images of separate sub-images of overlapping object areas are illustrated. The captured images in these figures were taken from a 5×5 pin hole array layer having a 12 micron diameter with 1000 micron spacing. FIGS. 13A and 13B illustrate restoral of a single image from overlapping sub-images, for example, those illustrated in FIGS. 12A-12C.

Figure 14:
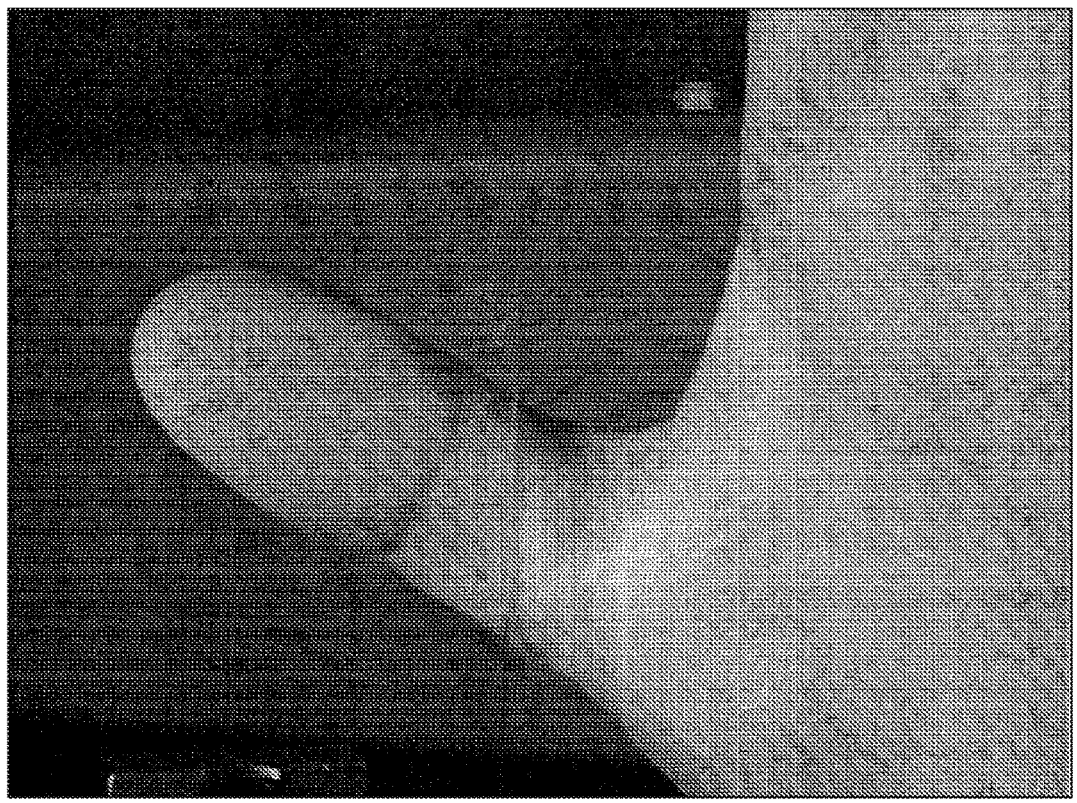
FIG. 14 is a captured image at a relatively low angle using a front illuminated prototype device.

Further tests were performed using a front illuminated prototype device that show that with respect to finger ridge imaging, contrast generally strongly depends on angle and wavelength. More particularly, with respect to a front illuminated prototype device the light source was positioned laterally adjacent the image sensor and was laterally adjusted for different angles of light. The same chromium mask as described with the prototype above was used to simulate an object to be sensed. Referring now to the image in FIG. 14, the ridge image contrast at 550 nm is relatively low when the light source angle is close to normal, for example.

Figure 15A:
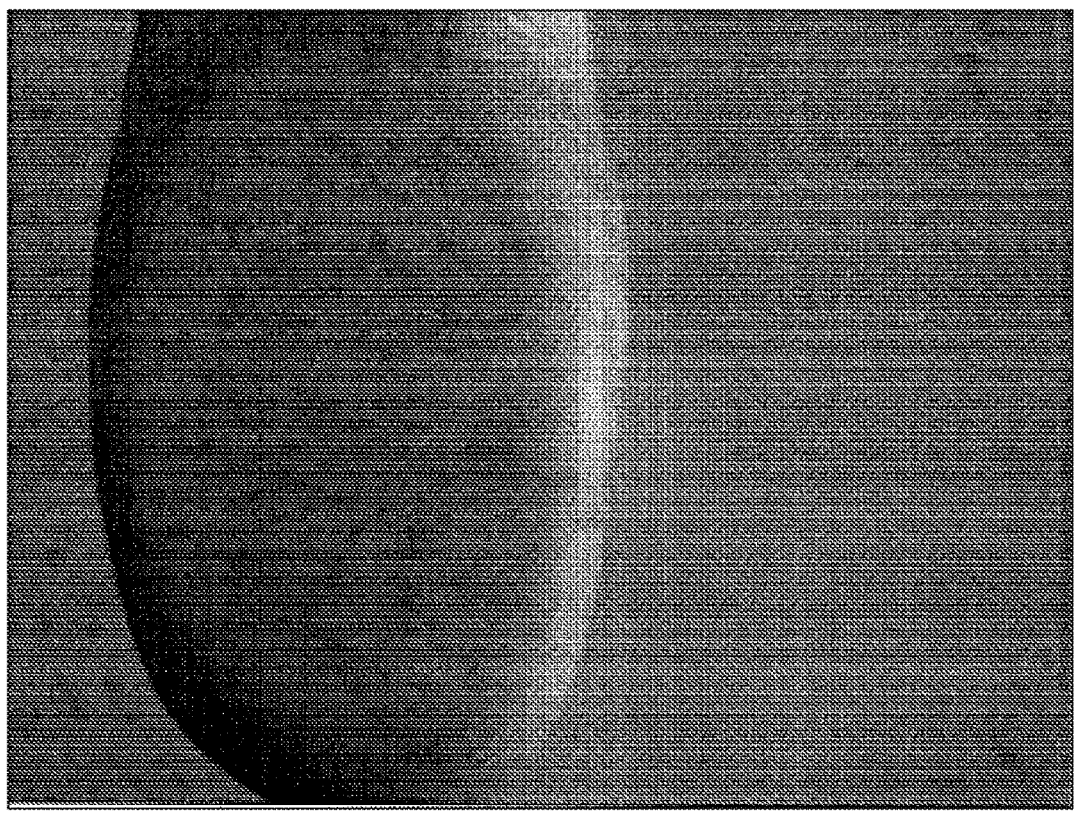
FIGS. 15a-15d are captured images using different colored light with the front illuminated prototype device.
Figure 15B:
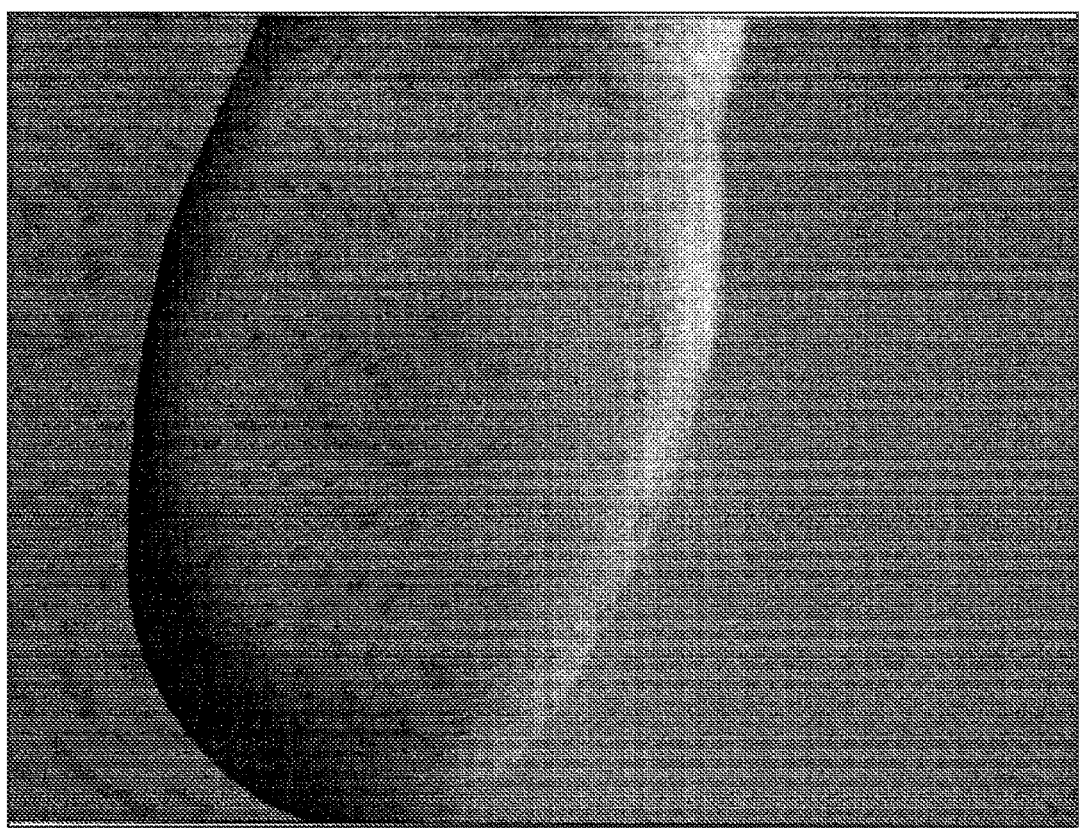
Figure 15C:
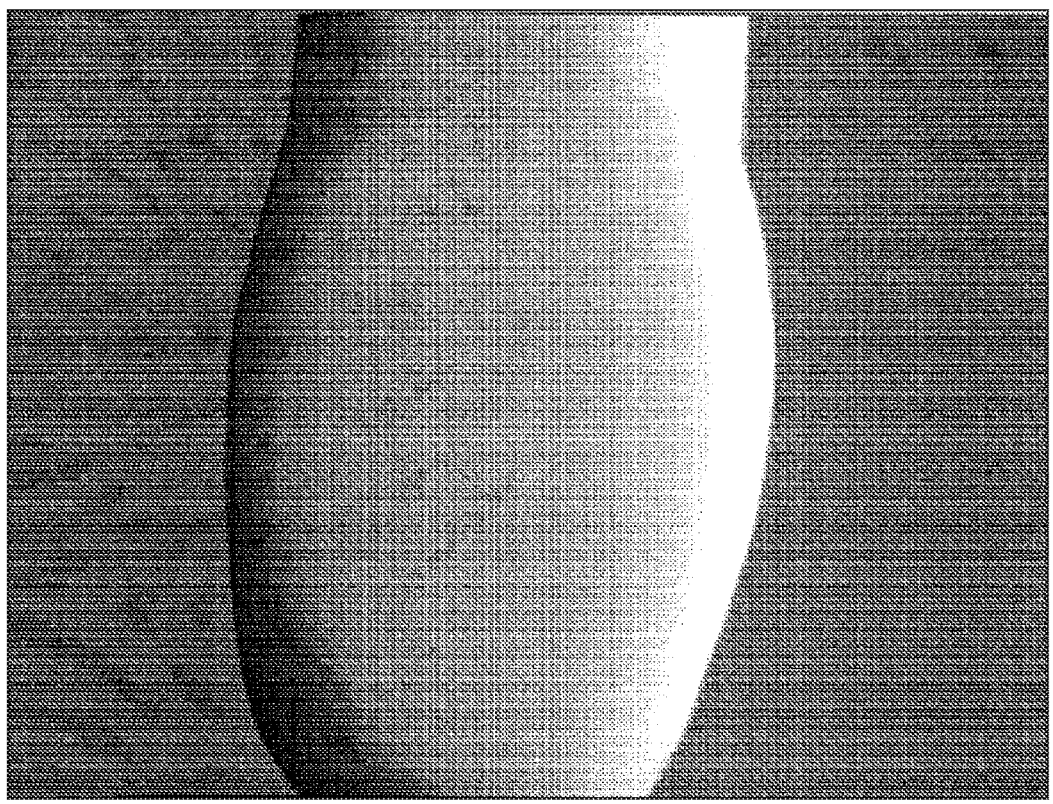
Figure 15D:
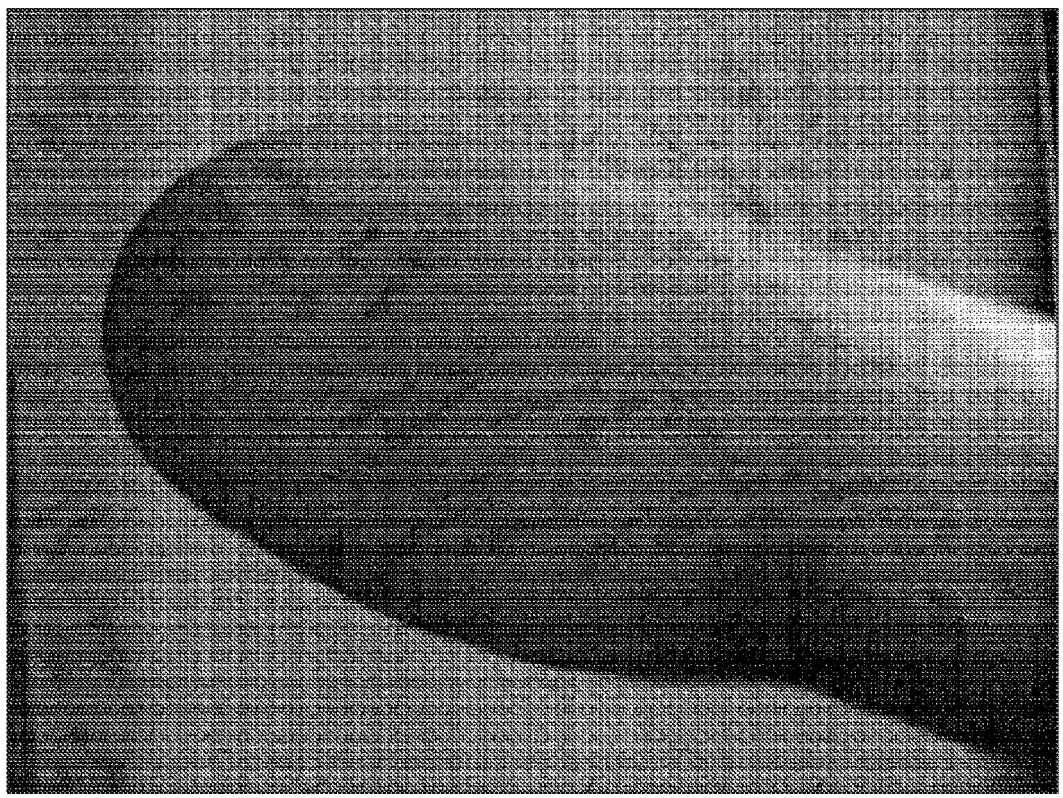
Figure 16A:
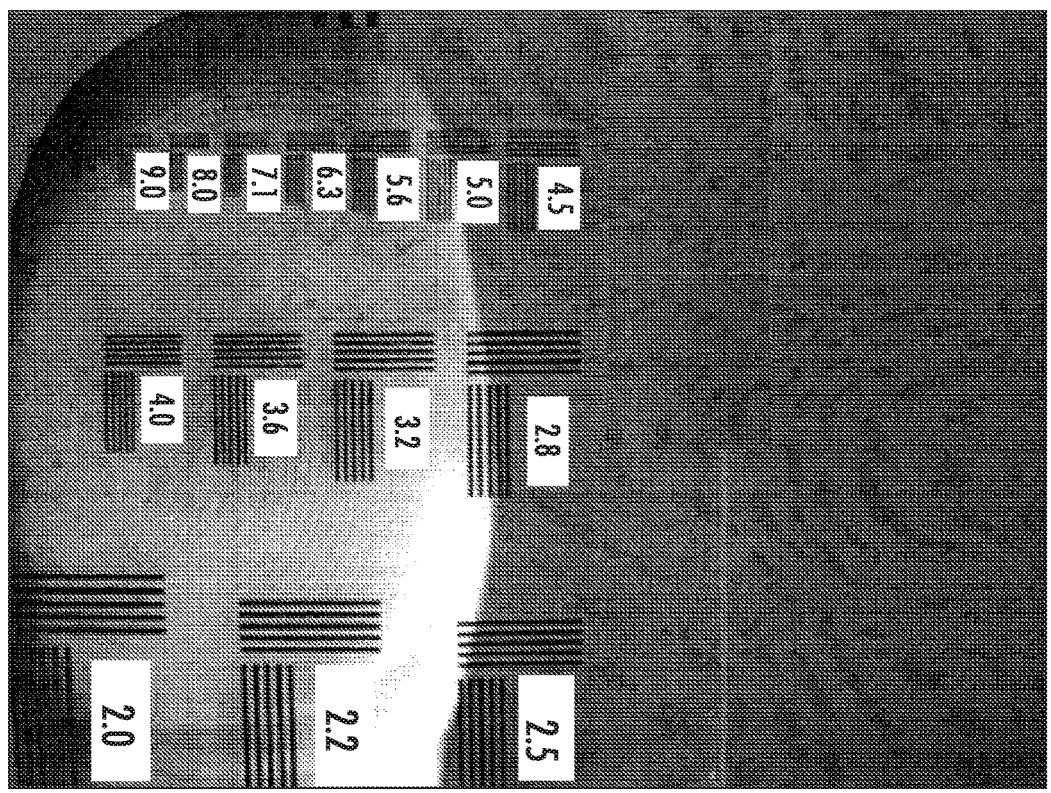
FIGS. 16a-16c are captured images at a relatively high angle using the front illuminated prototype device.
Figure 16B:
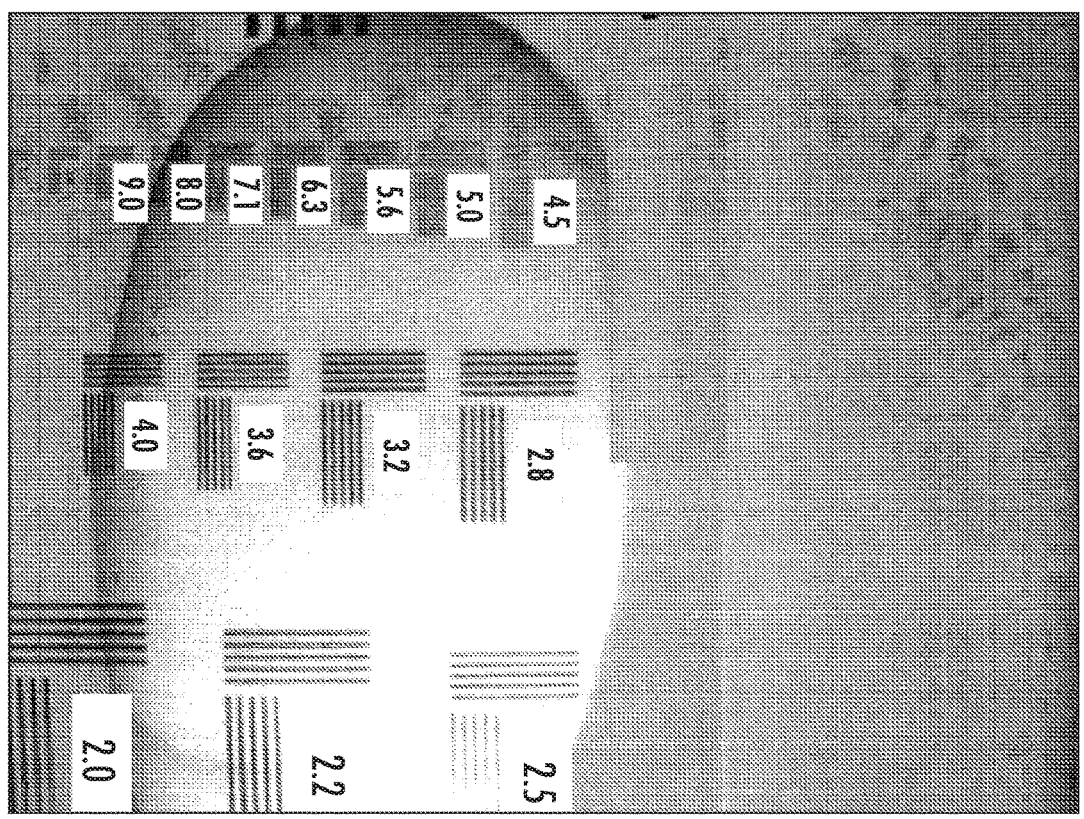
Figure 16C:
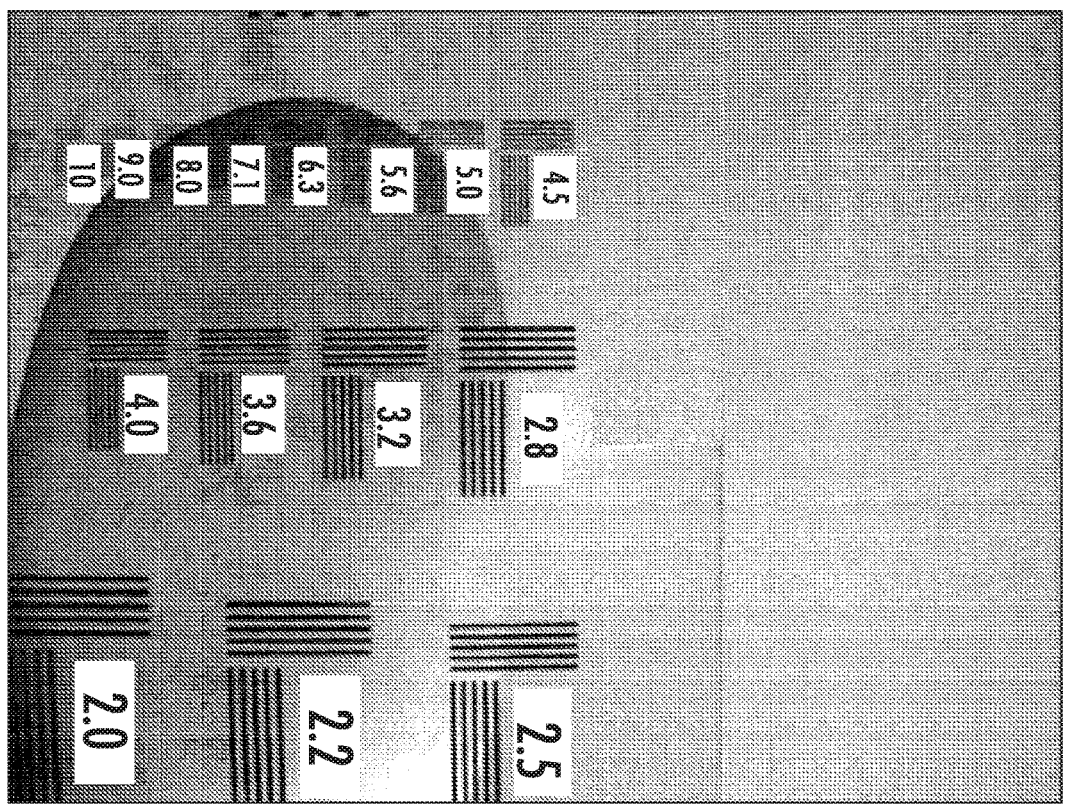
Figure 17A:
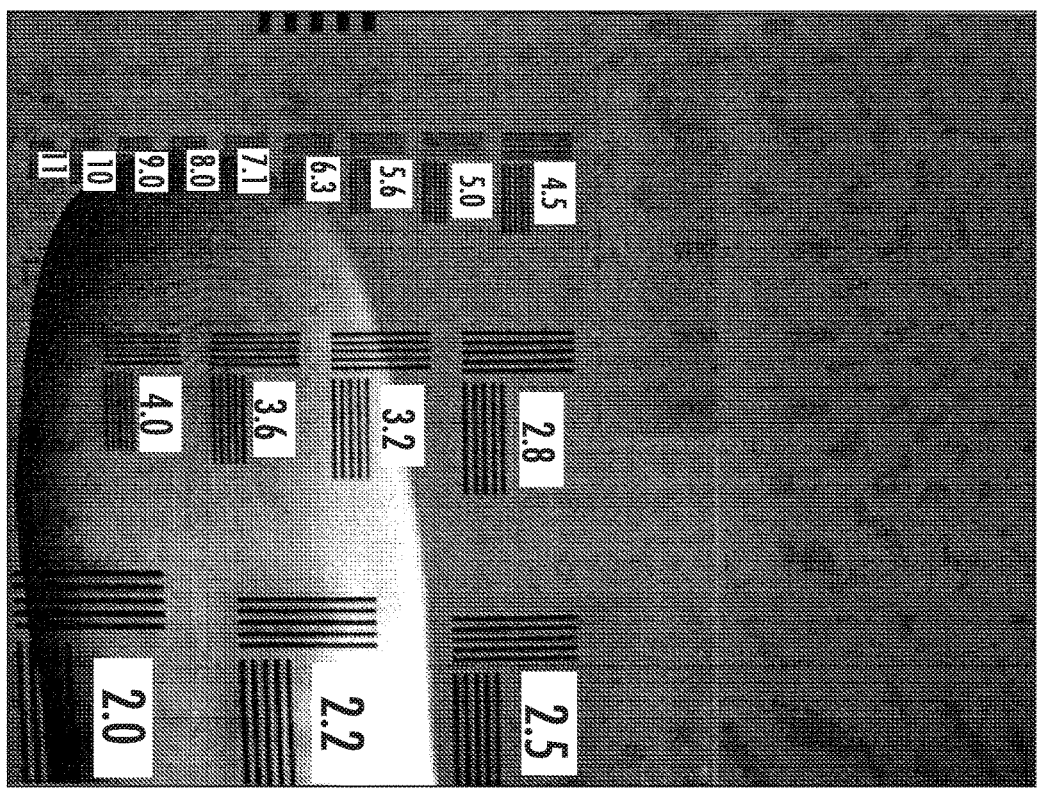
FIGS. 17a-17c are captured images at a relatively high angle using the front illuminated prototype device.
Figure 17B:
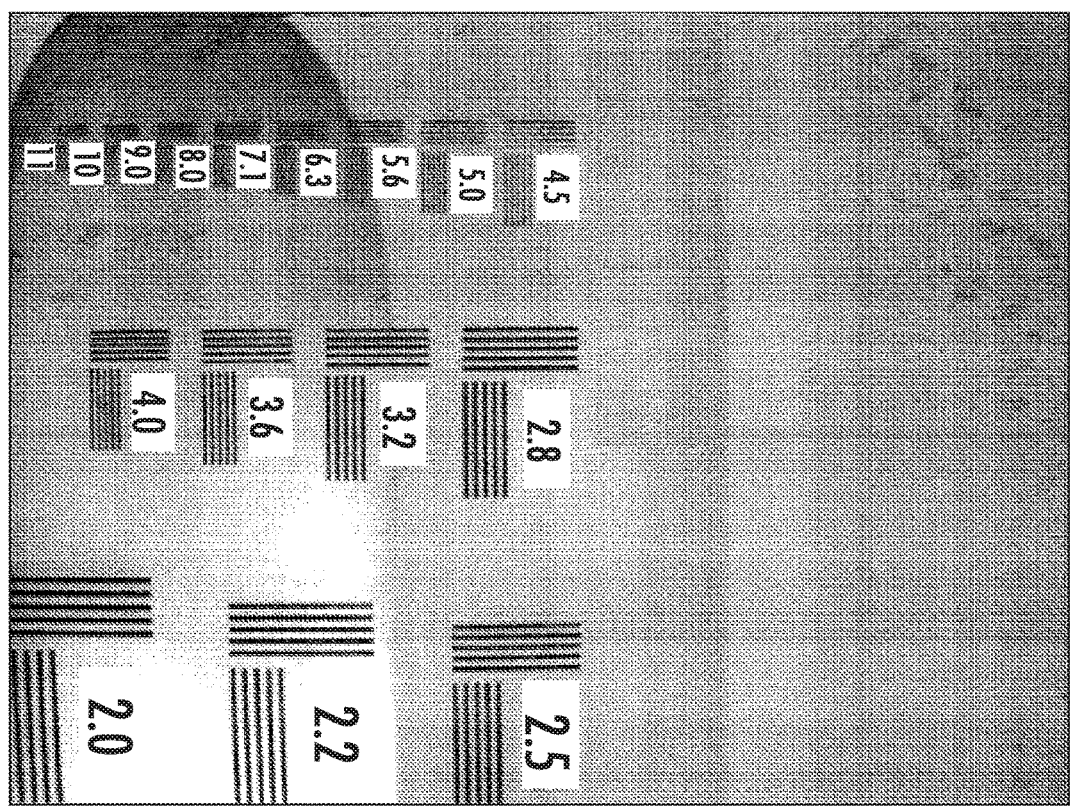
Figure 17C:
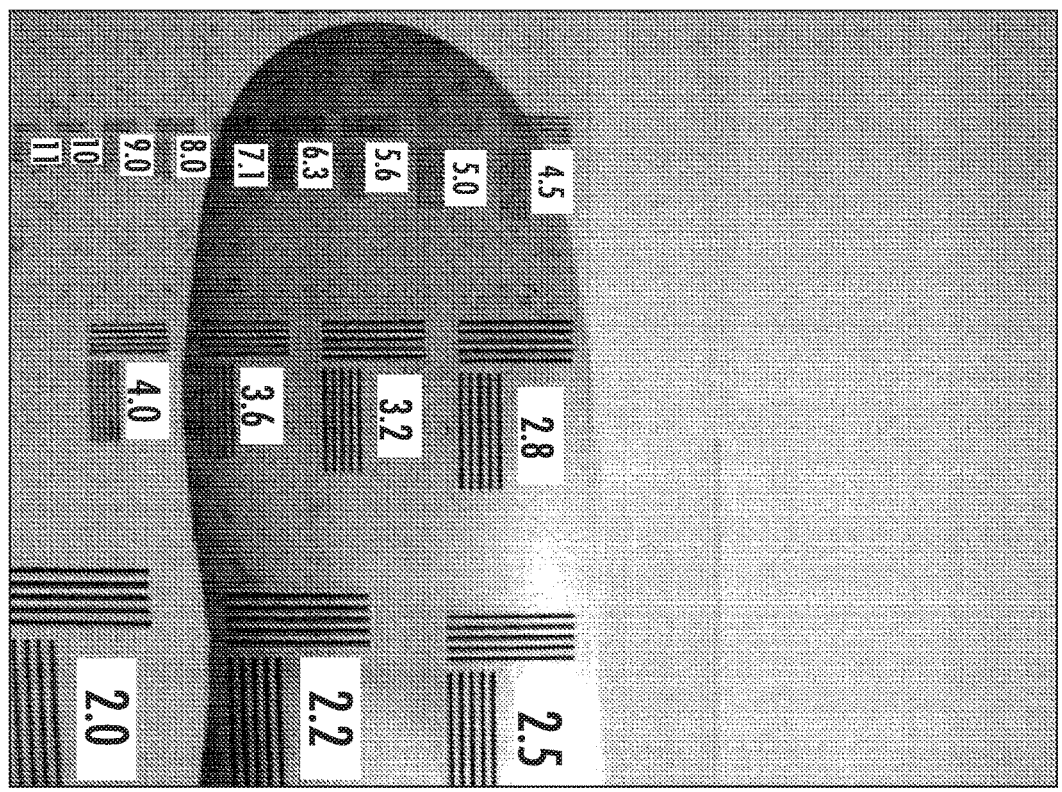
Figure 18A:
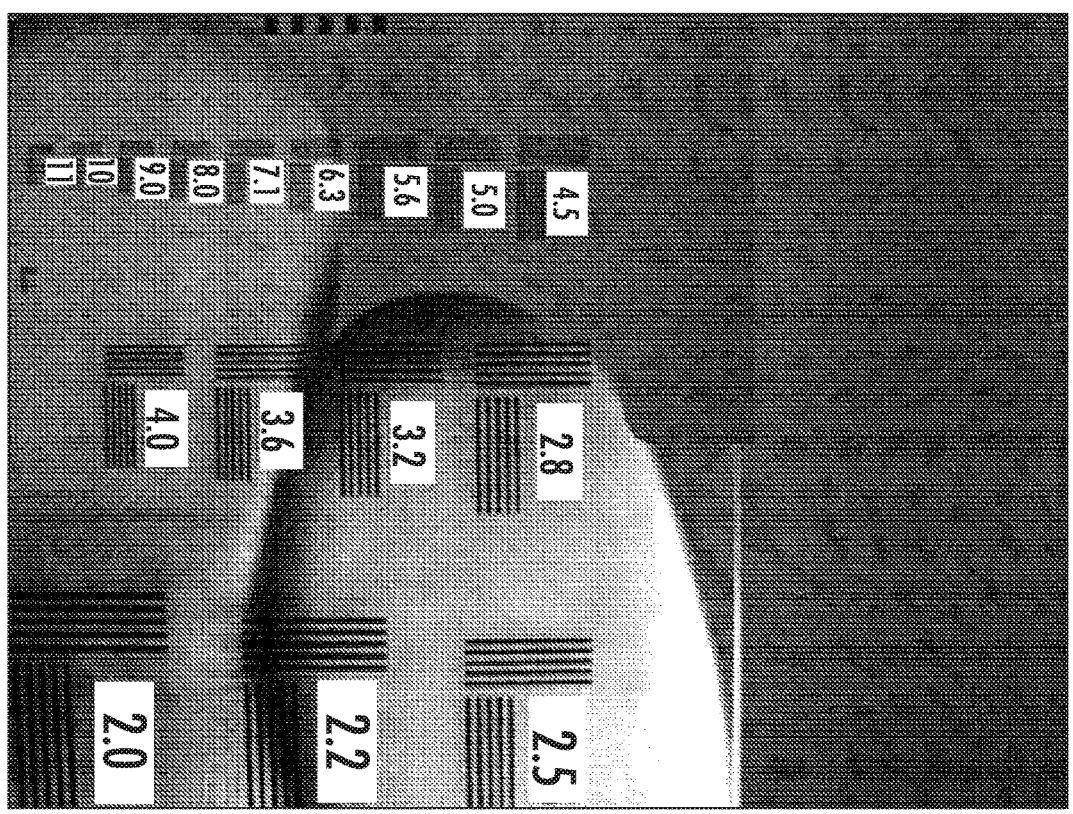
FIGS. 18a-18c are captured images at a relatively high angle using the front illuminated prototype device.
Figure 18B:
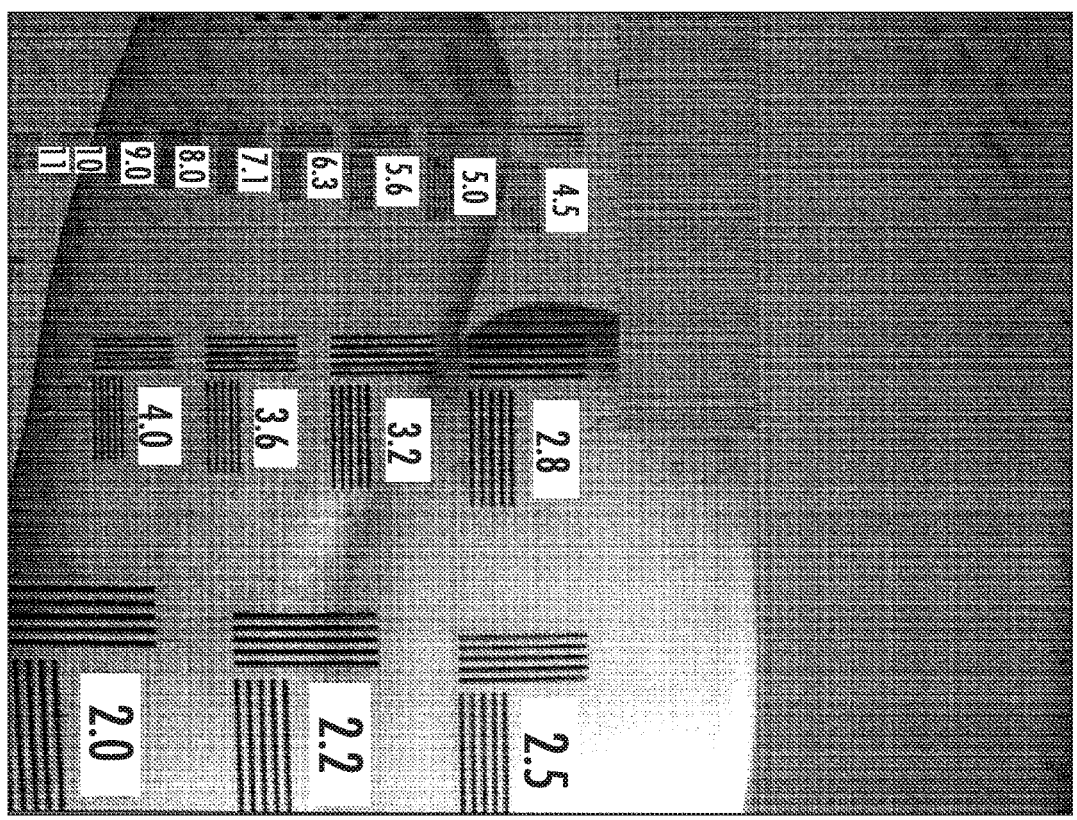
Figure 18C:
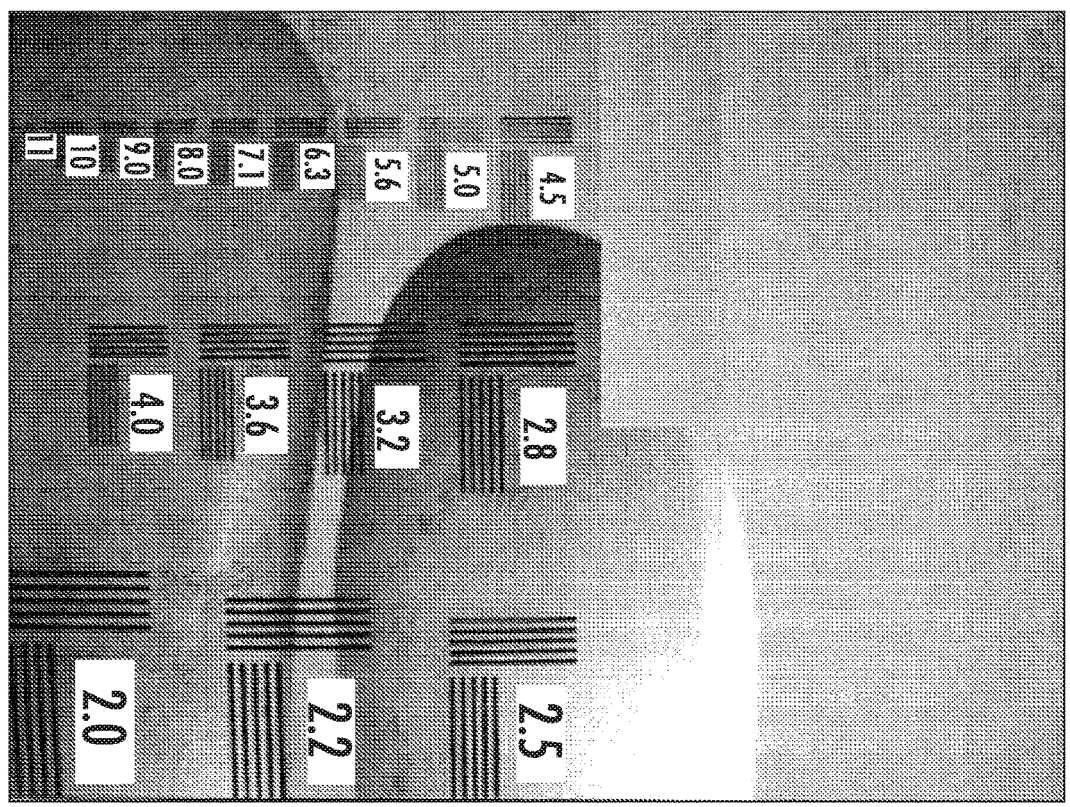

Referring now to FIGS. 15A-15D, the contrast with blue light (450 nm, FIG. 15A) or green light (550 nm, FIG. 15B) is illustratively better than with red light (650 nm, FIG. 15C) or infrared light (940 nm, FIG. 15D). FIGS. 16A-16C are captured images at a relatively high angle at 550 nm, 850 nm, and 940 nm, respectively. FIGS. 17A-17C and FIGS. 18A-18C are additional captured images at the relatively high angle at 550 nm, 850 nm, and 940 nm, respectively. Illustratively, the contrast is significantly improved at high angles, but still lower at infrared wavelengths. The ridge density is about 3 lines per millimeter.

While the electronic device 20 has been described herein as being in the form of a mobile wireless communications device, it should be understood by those skilled in the art that the electronic device may be in the form of a standalone optical image sensing device (i.e., a finger biometric sensing or fingerprint sensing device).

Moreover, while the optical image sensor 31 has been described primarily as being used for biometric authentication, it is understood that the optical image sensor, and more particularly, the image sensing circuitry, is capable of performing any or all of a biometric authentication function, spoof detection function, and a vital sign measurement function. In particular, the sensed 3D geometry of shadowing using the pin hole array mask layer 50, the multi-spectral nature of the imaging, and/or other characteristics of live fingers may be used for biometric authentication, for example. The optical image sensor 31 may also be capable of performing sensing other biometric features, such as, for example, heart or pulse rate (which may be used for determining a blood pressure), and/or pulse or blood oximetry, and may be based upon the ability of the sense images at different wavelengths. As will be appreciated by those skilled in the art, for detecting a heart rate, a combination of green and IR light may be used, and for detecting a blood oxygen level, a combination of red and IR light may be used.

Still further, the optical image sensor 31 may be used in combination with the openings 51 to operate in an ambient light sensing mode, which may be relatively desirable in wearable electronic devices, for example. More particularly, by using, for example, the entire pin hole array mask layer 50 and the entire pixel array of the optical image sensor 31, a relatively high angle of light acceptance may result, which is generally desirable for ambient light sensing operations.

Further details of the operation of the ambient light sensing mode will now be described. All pixels may be combined into a single output, and read out with extremely low power consumption readout circuitry. The optical image sensor 31 in combination with the pin hole array mask layer 50 may then integrate light in very wide field of view (FOV), for example, up to 180 degrees. A typical camera, for example, senses light in a relatively narrow FOV, typically between 60 and 70 degrees, which may be too small for operation in an ambient light sensing mode. By having a very large, for example, up to 180 degree FOV for the pin hole array mask layer 50 in combination with the optical image sensor 31 may provide a relatively large advantage over a typical camera, for example.

The use of the pin hole array mask layer 50, or even pinhole imaging techniques, provides wide-angle light sensing since the pinholes or openings 51 are located relatively close to the optical image sensor 31. The effective focal length is thus significantly lower than the size of the optical image sensor 31. When the pixels are combined in a single output, it would be sensitive to nearly all the light entering the openings 51. This allows a relatively low-power ambient light sensing mode that would have a stability advantage over typical sensors due to the reduced orientation dependence, for example.

Figure 19:
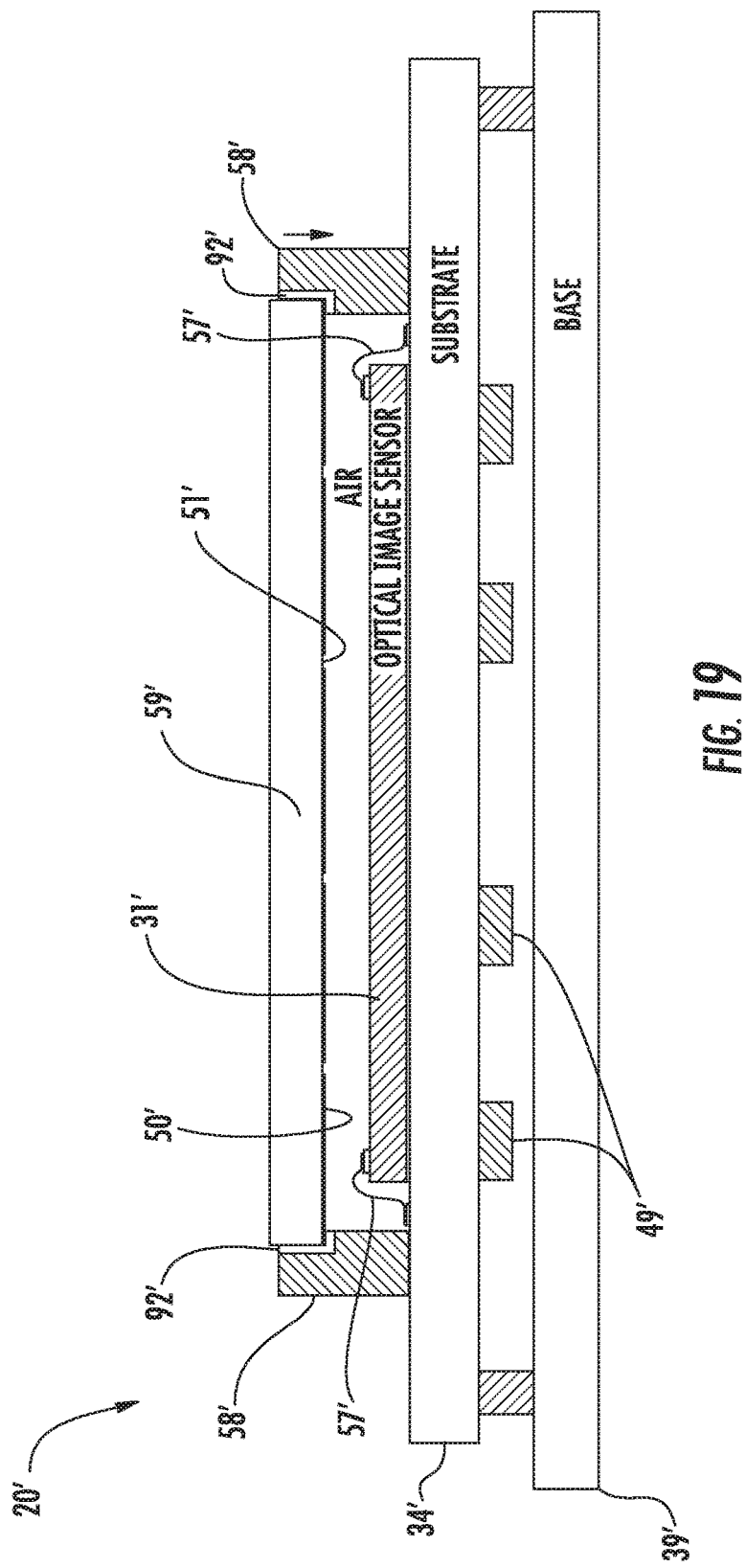
FIG. 19 is a schematic cross-sectional view of a portion of an electronic device according to another embodiment of the present invention.

Referring now to FIG. 19, a portion of an electronic device 20' illustrating an exemplary integration design. A substrate 34' is spaced from a base 39'. Passive components 49' are carried by a lower surface of the substrate 34'. The optical image sensor 31' is carried by an upper surface of the substrate 34'. Bond wires 57' couple the optical image sensing circuitry to circuitry carried by the substrate 34'. An enclosure 58' extends upwardly from the substrate 34' around the optical image sensor 31'. A transparent glass layer 59' is carried by the enclosure, and has a thickness, for example, of 0.5 mm. A pin hole array mask layer 50' is carried by a lower surface of the transparent layer 59', for example, a glass layer. The enclosure 58' spaces the pin hole array mask layer 50' and the transparent glass layer 59' from the optical image sensor 31', for example, by a distance of 150 microns defining an air gap therebetween. A light absorptive adhesive 92', for example, epoxy, may secure the transparent glass layer 59' and the pin hole array mask layer 50' to the enclosure 58'.

Referring now to FIG. 20, the components or elements illustrated in FIG. 19 are integrated into an exemplary electronic device 20'. A printed circuit board (PCB) 81' couples the substrate 34', and more particularly, the lower surface of the substrate adjacent the passive components 49'. A display layer 36' including spaced apart display pixels 38' is carried by the upper surface of the substrate 34' laterally adjacent, or around, the enclosure 58'. The display layer 36' may be coupled to display control circuitry 82' carried off the substrate 34'. A transparent cover layer 46' is over the transparent layer 59'. The transparent cover layer 46' may be secured to the transparent layer 59' with an adhesive, for example. The transparent cover layer 46' may be glass or onyx, for example, or may be another material.

A method aspect is directed to a method of making an electronic device 20. The method includes positioning a pin hole array mask layer 50 above an optical image sensor 31, and positioning a display layer 36 above the pin hole array mask layer. The display layer 36 includes spaced apart display pixels 38. The method also includes positioning a transparent cover layer 46 above the display layer 36 defining a finger placement surface 47 capable of receiving a user's finger 40 adjacent thereto.

Another method aspect is directed to a method of sensing an optical image. The method includes using an optical image sensor 31 to sense light reflected from a user's finger 40 adjacent a finger placement surface 47 defined by a transparent cover layer 46, through the transparent cover layer, through a pin hole array mask layer 50 above the optical image sensor, and through a display layer 36 above the pin hole array mask layer, wherein the display layer includes spaced apart display pixels 38.

Referring now to FIG. 21, in another embodiment, the pin hole array mask layer 50" including the openings 51" may not be between the optical image sensor 31" and the display layer 36", but instead, carried by or integrated with the display layer. Illustratively, the display layer 36" includes an array of spaced apart display pixels 38" and/or micro-lenses for displaying images and which are spaced apart to allow light to pass through. The spacing between the display pixels 38", which allows the light to pass through, defines the openings 51". This is in contrast to embodiments where the space between the spaced apart display pixels 38 may be aligned with the openings 51 or pin holes in the pin hole array mask layer 50. Method aspects are directed to a method of making a related electronic device and a method of using or sensing a finger using the electronic device.

Referring now to FIG. 22, in yet another embodiment, the pin hole array mask layer 50''' includes lenses 91''' in the openings 51'''. Each of the lenses 91''' may have a diameter of about 40-100 microns, for example. The lenses 91''' may advantageously improve image quality and the SNR, which may thus reduce optical power for illumination and total overall power consumption, which may be particularly, advantageous when used with mobile or portable devices. Lenses may alternatively or additionally be included in the display layer 36'''.

The benefits of biometric data collected by a device as disclosed herein include convenient access to device features without the use of passwords. In other examples, user biometric data is collected for providing users with feedback about their health or fitness levels. The present disclosure further contemplates other uses for personal information data, including biometric data, that benefit the user of such a device.

Practicing the present invention requires that collecting, transferring, storing, or analyzing user data, including personal information, will comply with established privacy policies and practices. In particular, such entities should implement and consistently use privacy policies and practices that are generally recognized as meeting or exceeding industry or governmental requirements for maintaining personal information data private and secure, including the use of data encryption and security methods that meets or exceeds industry or government standards. Personal information from users should not be shared or sold outside of legitimate and reasonable uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

The present disclosure also contemplates the selective blocking of access to, or use of, personal information data, including biometric data. Hardware and/or software elements disclosed herein can be configured to prevent or block access to such personal information data. Optionally allowing users to bypass biometric authentication steps by providing secure information such as passwords, personal identification numbers (PINS), touch gestures, or other authentication methods, alone or in combination, is well known to those of skill in the art. Users can further select to remove, disable, or restrict access to certain health-related applications collecting users' personal health or fitness data.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An electronic device comprising:
   an optical image sensor;
   a pin hole array mask layer above the optical image sensor;
   a display layer above the pin hole array mask layer comprising a plurality of spaced apart light emitting diodes (LEDs); and
   a transparent cover layer above the display layer defining a finger placement surface capable of receiving a finger adjacent thereto;
   the plurality of spaced apart LEDs providing illumination for the optical image sensor, and being aligned with the pin hole array mask layer so that light reflected from the finger adjacent the finger placement surface passes through the pin hole array mask layer and between the plurality of spaced apart LEDs to the optical image sensor.

2. The electronic device of claim 1 wherein the plurality of spaced apart LEDs comprises at least one of visible light LEDs, infrared light LEDs, and ultraviolet light LEDs.

3. The electronic device of claim 1 wherein the optical image sensor, pin hole array mask layer, and finger placement surface are configured to define overlapping areas at the finger placement surface, and spaced apart areas at the optical image sensor.

4. The electronic device of claim 1 wherein the pin hole array mask layer has a plurality of openings each having a size in a range of 5-40 microns.

5. The electronic device of claim 1 wherein the pin hole array mask layer has a plurality of openings spaced from one another by a distance in a range of 1-3 millimeters.

6. The electronic device of claim 1 wherein the pin hole array mask layer is spaced from the optical image sensor by a distance in a range of 100-300 microns.

7. The electronic device of claim 1 wherein the pin hole array mask layer is spaced from the finger placement surface by a distance in a range of 1500-2000 microns.

8. The electronic device of claim 1 wherein the pin hole array mask layer comprises chromium.

9. The electronic device of claim 1 further comprising a flexible circuit substrate carrying the optical image sensor.

10. The electronic device of claim 1 further comprising an optically transparent body between the optical image sensor and the pin hole array mask layer.

11. The electronic device of claim 1 further comprising an optically clear adhesive layer above the optical image sensor.

12. The electronic device of claim 1 wherein the optical image sensor is capable of performing at least one of an authentication function, a spoof detection function, a navigation function, and a vital sign measurement function.

13. The electronic device of claim 1 wherein the optical image sensor is capable of performing an ambient light measurement.

14. The electronic device of claim 1 wherein the optical image sensor is capable of performing an authentication function based upon a fingerprint from the finger.

15. The electronic device of claim 1 wherein the display layer comprises a touch display layer.

16. The electronic device of claim 1 wherein the pin hole array mask layer has a plurality of spaced apart openings therein; and wherein the pin hole array mask layer comprises a plurality of lenses within the plurality of openings.

17. An electronic device comprising:
    an optical image sensor;
    a display layer above the optical image sensor and comprising a plurality of spaced apart light emitting diodes (LEDs) and having a plurality of pin holes therebetween; and
    a transparent cover layer above the display layer defining a finger placement surface capable of receiving a finger adjacent thereto;
    the plurality of spaced apart LEDs providing illumination for the optical image sensor, and being aligned with the pin holes so that light reflected from the finger adjacent the finger placement surface passes through the pin holes and between the plurality of spaced apart LEDs to the optical image sensor.

18. The electronic device of claim 17 wherein the plurality of spaced apart LEDs comprises at least one of visible light LEDs, infrared light LEDs, and ultraviolet light LEDs.

19. The electronic device of claim 17 wherein the optical image sensor, the plurality of pin holes, and finger placement surface are configured to define overlapping areas at the finger placement surface, and spaced apart areas at the optical image sensor.

20. The electronic device of claim 17 wherein the plurality of pin holes each have a size in a range of 5-40 microns.

21. The electronic device of claim 17 wherein the plurality of pin holes are spaced from one another by a distance in a range of 1-3 millimeters.

22. The electronic device of claim 17 further comprising an optically clear adhesive layer above the optical image sensor.

23. The electronic device of claim 17 wherein the optical image sensor is capable of performing at least one of an authentication function, a spoof detection function, and a vital sign measurement function.

24. A method of using an electronic device comprising:
using a plurality of spaced apart light emitting diodes (LEDs) of a display layer to direct light into a finger when adjacent a transparent cover layer defining finger placement surface capable of receiving the finger adjacent thereto; and
using an optical image sensor to sense reflected light from the finger adjacent the finger placement surface, the reflected light being sensed through a pin hole array mask layer above the optical image sensor, the display layer being above the pin hole array mask layer, the display layer comprising the plurality of spaced apart LEDs, and the transparent cover layer above the display layer;
the plurality of spaced apart LEDs providing illumination for the optical image sensor, and being aligned with the pin hole array mask layer so that light reflected from the finger adjacent the finger placement surface passes through the pin hole array mask layer and between the plurality of spaced apart LEDs to the optical image sensor.

25. The method of claim 24 wherein the plurality of spaced apart LEDs comprises at least one of visible light LEDs, infrared light LEDs, and ultraviolet light LEDs.

26. The method of claim 24 wherein the optical image sensor, pin hole array mask layer, and finger placement surface define overlapping areas at the finger placement surface, and spaced apart areas at the optical image sensor.

27. The method of claim 24 wherein the pin hole array mask layer has a plurality of openings each having a size in a range of 5-40 microns.

28. The method of claim 24 wherein the pin hole array mask layer has a plurality of openings spaced from one another by a distance in a range of 1-3 millimeters.

29. The method of claim 24 wherein the pin hole array mask layer is spaced from the optical image sensor by a distance in a range of 100-300 microns.

30. The method of claim 24 wherein the pin hole array mask layer is spaced from the finger placement surface by a distance in a range of 1500-2000 microns.

* * * * *